(12) United States Patent
Bernshtein

(10) Patent No.: US 10,076,433 B1
(45) Date of Patent: Sep. 18, 2018

(54) INTRAVASCULAR BIFURICATION ZONE IMPLANTS AND CRIMPING AND DEPLOYMENT METHODS THEREOF

(71) Applicant: Vadim Bernshtein, Haifa (IL)

(72) Inventor: Vadim Bernshtein, Haifa (IL)

( * ) Notice: Subject to any disclaimer, the term of this patent is extended or adjusted under 35 U.S.C. 154(b) by 0 days.

(21) Appl. No.: 15/879,462

(22) Filed: Jan. 25, 2018

Related U.S. Application Data

(60) Provisional application No. 62/502,770, filed on May 8, 2017.

(51) Int. Cl.
| | |
|---|---|
| *A61F 2/954* | (2013.01) |
| *A61F 2/07* | (2013.01) |
| *A61F 2/962* | (2013.01) |
| A61F 2/06 | (2013.01) |

(52) U.S. Cl.
CPC ........... *A61F 2/954* (2013.01); *A61F 2/07* (2013.01); *A61F 2/962* (2013.01); *A61F 2002/061* (2013.01); *A61F 2002/065* (2013.01); *A61F 2002/077* (2013.01); *A61F 2220/0016* (2013.01)

(58) Field of Classification Search
CPC .... A61F 2/954; A61F 2/07; A61F 2/95; A61F 2/966; A61F 2/962; A61F 2/856; A61F 2/82; A61F 2002/061; A61F 2002/065; A61F 2002/067; A61F 2250/0039; A61F 2/86; A61F 2002/826
USPC .............. 606/108; 623/1.11–1.13, 1.15, 1.35
See application file for complete search history.

(56) References Cited

U.S. PATENT DOCUMENTS

| | | | |
|---|---|---|---|
| 7,074,235 B1 * | 7/2006 | Roy | A61F 2/06 606/108 |
| 8,702,788 B2 | 4/2014 | Kheradvar et al. | |
| 9,101,457 B2 | 8/2015 | Benary | |
| 9,101,500 B2 | 8/2015 | Feld et al. | |

(Continued)

OTHER PUBLICATIONS

S. Oderich et al. "Technical Aspects of Repair of Juxtarenal Abdominal Aortic Aneurysms using the Zenith Fenestrated Endovascular Atent Graft", Journal of Vascular Surgery 2014;59:1456-61.

(Continued)

*Primary Examiner* — Katherine M Shi
(74) *Attorney, Agent, or Firm* — 1st-Tech-Ideas.com; Haim M. Factor

(57) ABSTRACT

A multi stent delivery system for intravascular bifurcation zone delivery and deployment of a multi stent, the bifurcation zone having a main blood vessel, the main blood vessel having a main blood vessel longitudinal axis and at least one side blood vessel inclined/branching out of the main blood vessel, the delivery system comprising: a catheter having a catheter longitudinal axis substantially coaxial with the main blood vessel longitudinal axis, a tube positioned coaxially within the catheter, the catheter having a distal end and a proximal end, and the tube containing: at least one crimped side stent for deployment substantially normal to the catheter longitudinal axis and into the side blood vessel; and at least one crimped main stent for deployment substantially along the catheter longitudinal axis into the main blood vessel; wherein the at least one crimped side stent and at least one crimped main stent are part of a unified/singular configuration within a sheath, located substantially at the distal end.

7 Claims, 24 Drawing Sheets

(56) References Cited

U.S. PATENT DOCUMENTS

| | | |
|---|---|---|
| 9,492,297 B2 | 11/2016 | Pallazza |
| 9,610,182 B2 | 4/2017 | Douglas |
| 9,730,821 B2 | 8/2017 | Bourang et al. |
| 9,737,424 B2 | 8/2017 | Bourang et al. |
| 2007/0244547 A1* | 10/2007 | Greenan .................. A61F 2/07 623/1.35 |

OTHER PUBLICATIONS

A. Kitagawa et al, "Zenith p-branch Standard Fenestrated Endovascular Graft for Juxtarenal Abdominal Aortic Aneurysms", Society for Vascular Surgery, 2013.

R. K. Greenberg et al., "Intermediate Results of a United States Multicenter Trial of Fenestrated Endograft Repair for Juxtarenal Abdominal Aortic Aneurysms", J Vasc Surg for FEVAR, 2009.

T. M. Mastracci et al., "Durability of Branches in Branched and Fenestrated Endografts", J Vasc Surgery, 2013.

T. Martin-Gonzalez et al., "Renal Outcomes Following Fenestrated and Branched Endografting", Eur Journal of Vascular Endovascular Surg, 2015.

\* cited by examiner

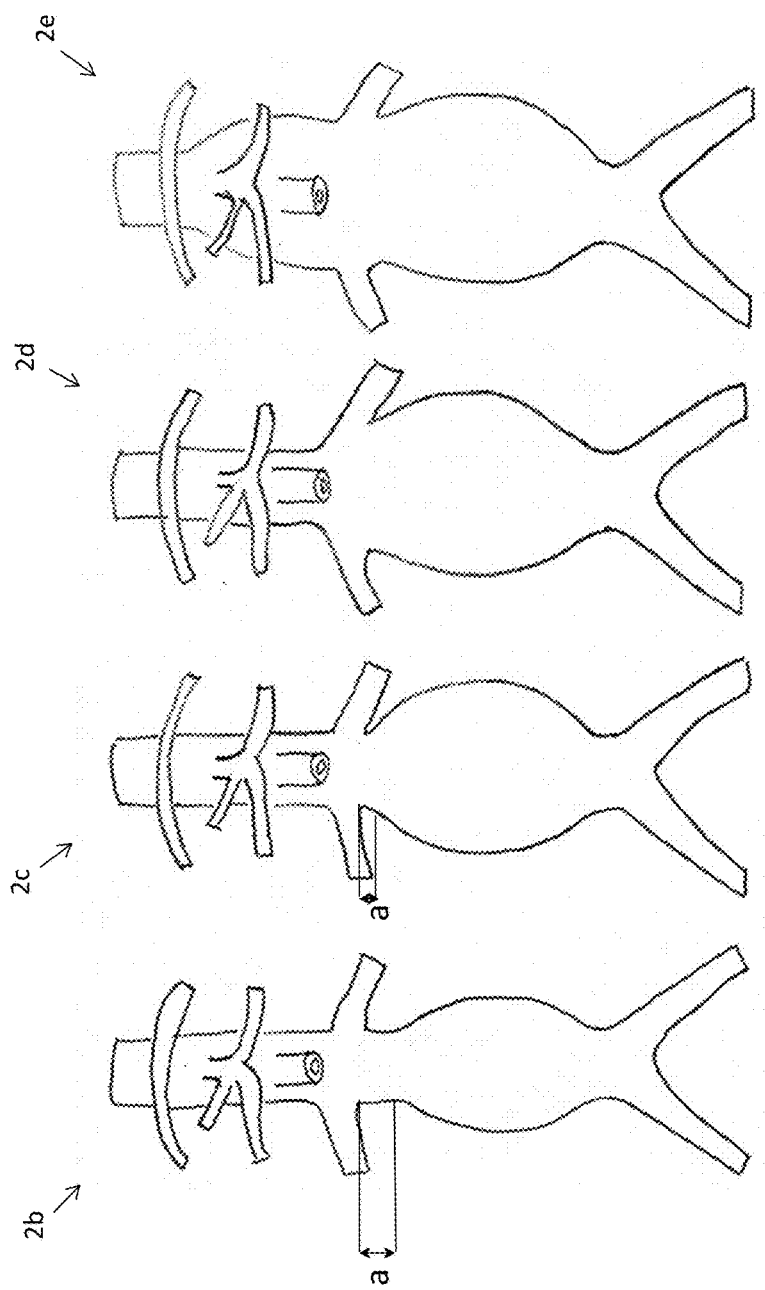

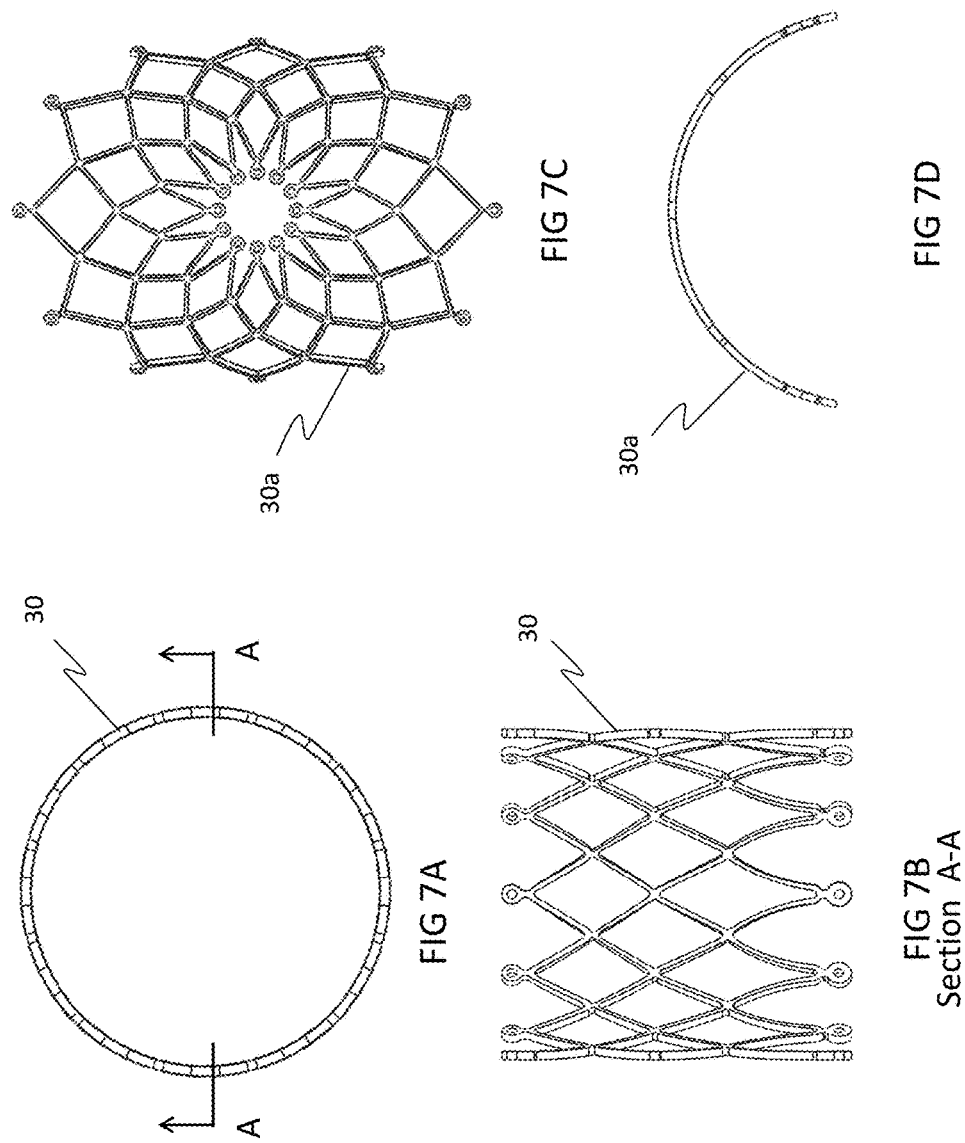

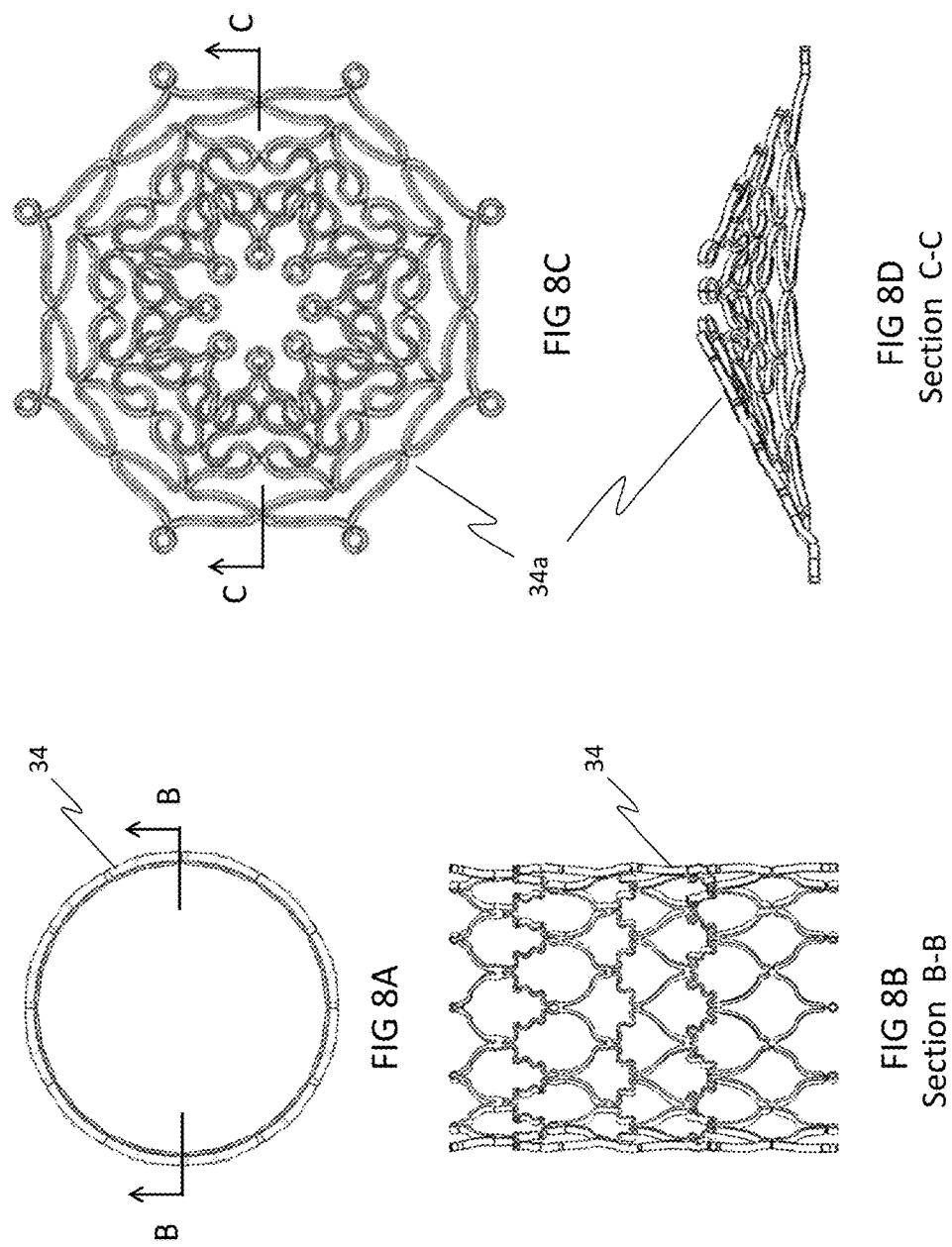

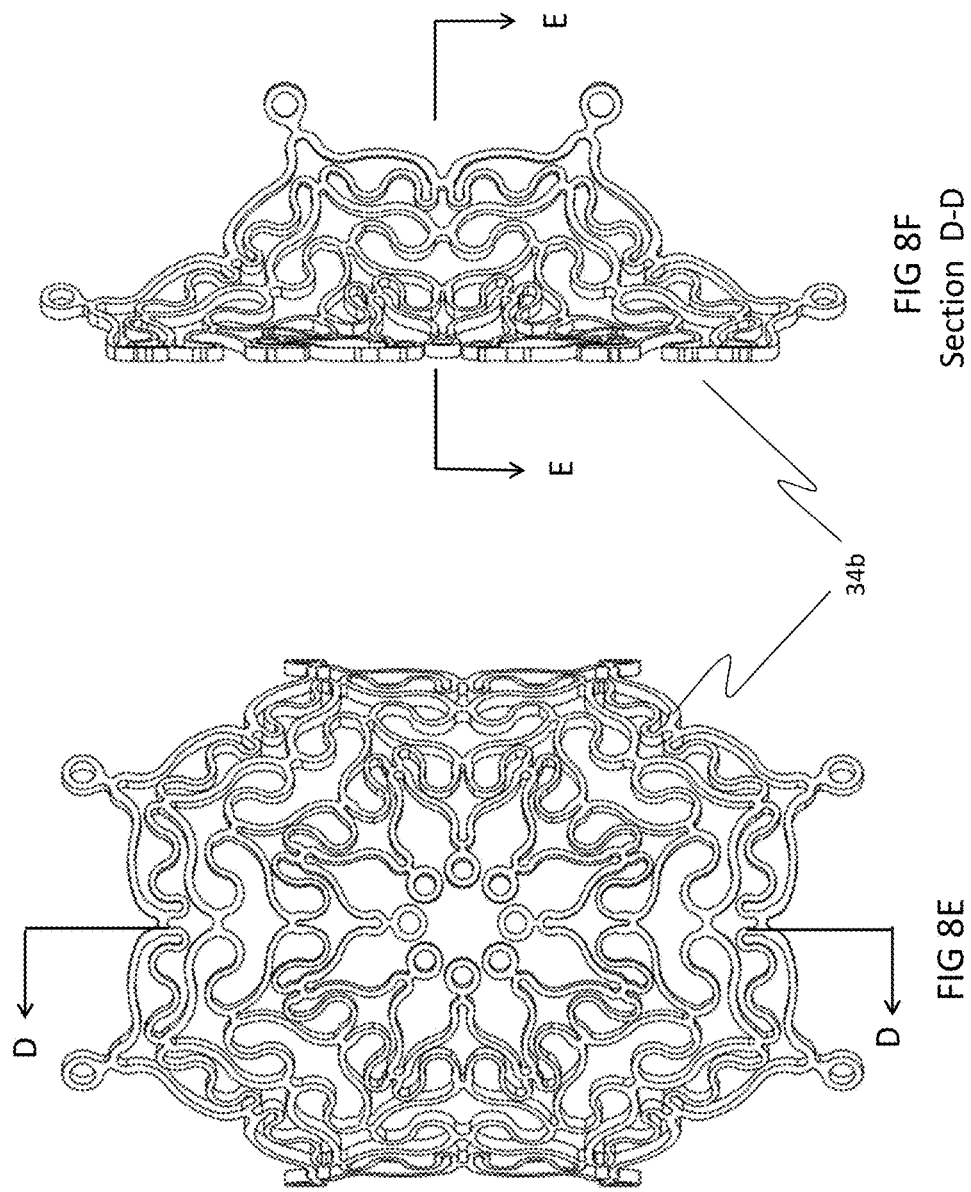

Section E-E

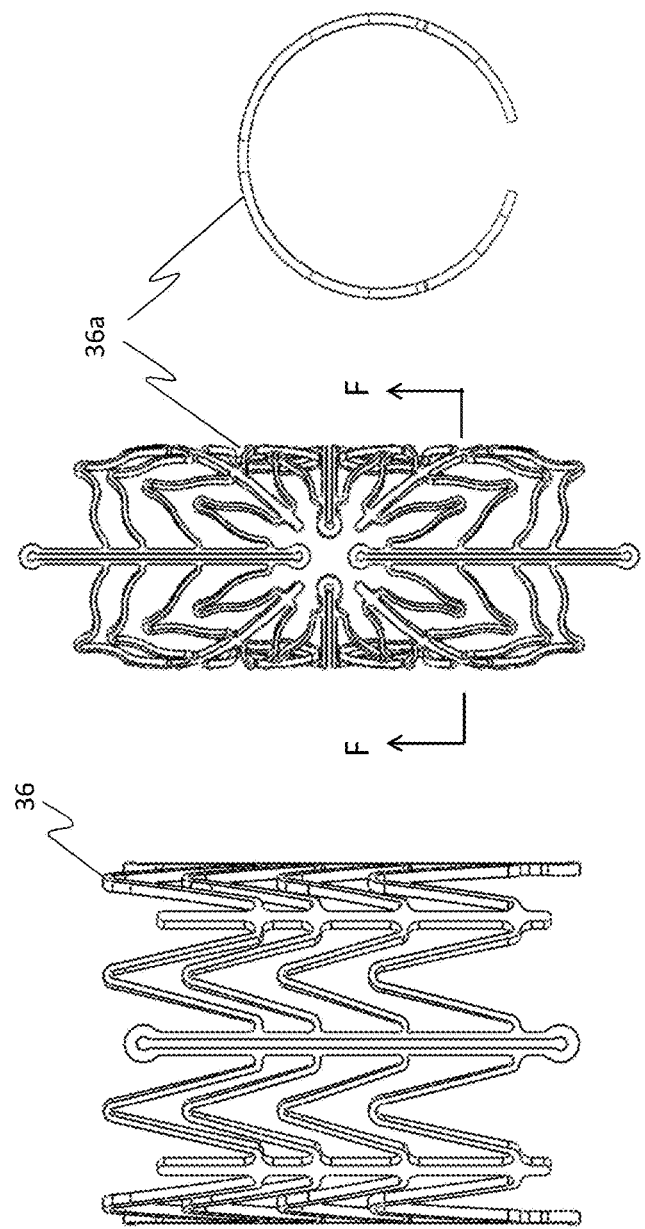

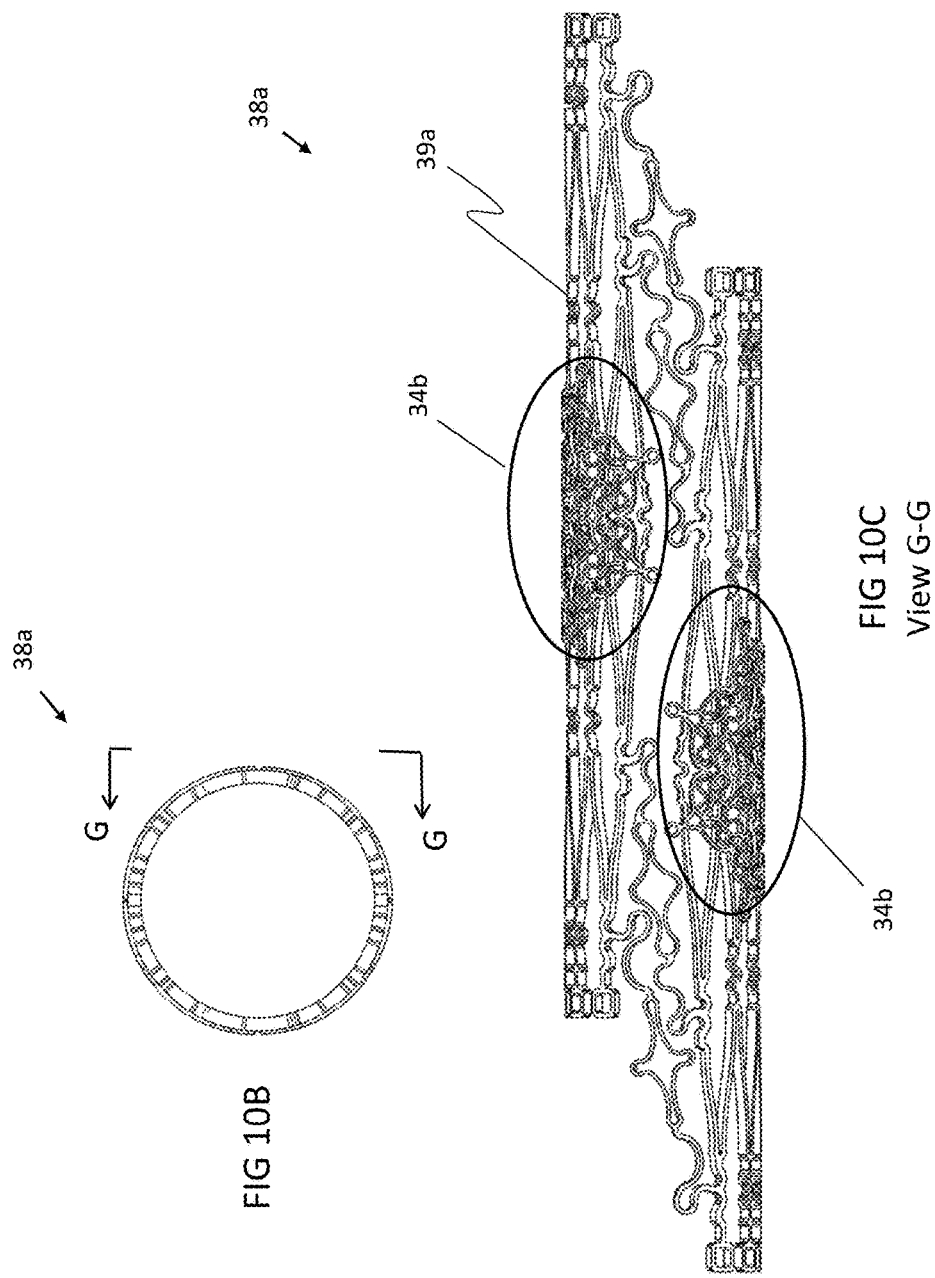

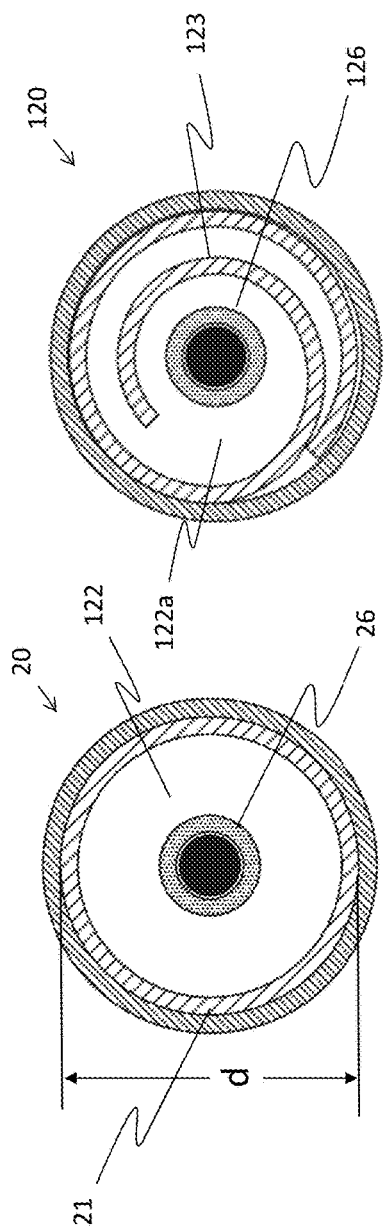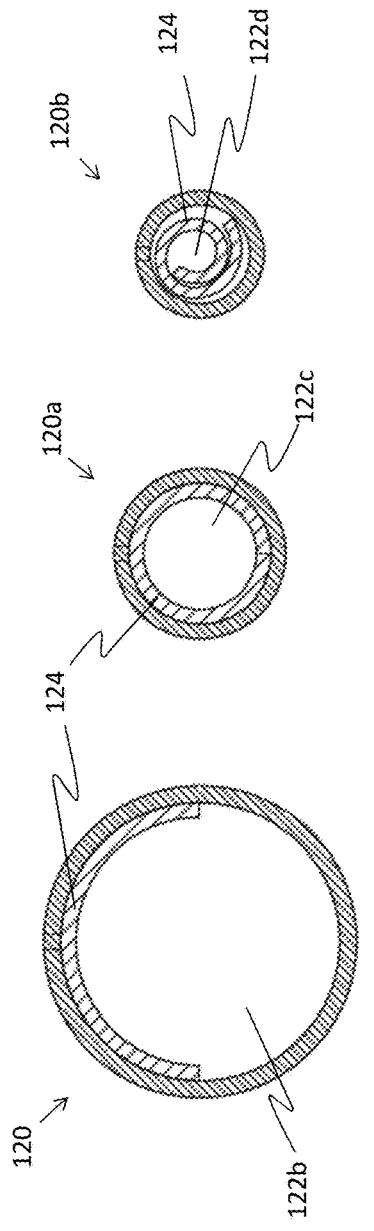

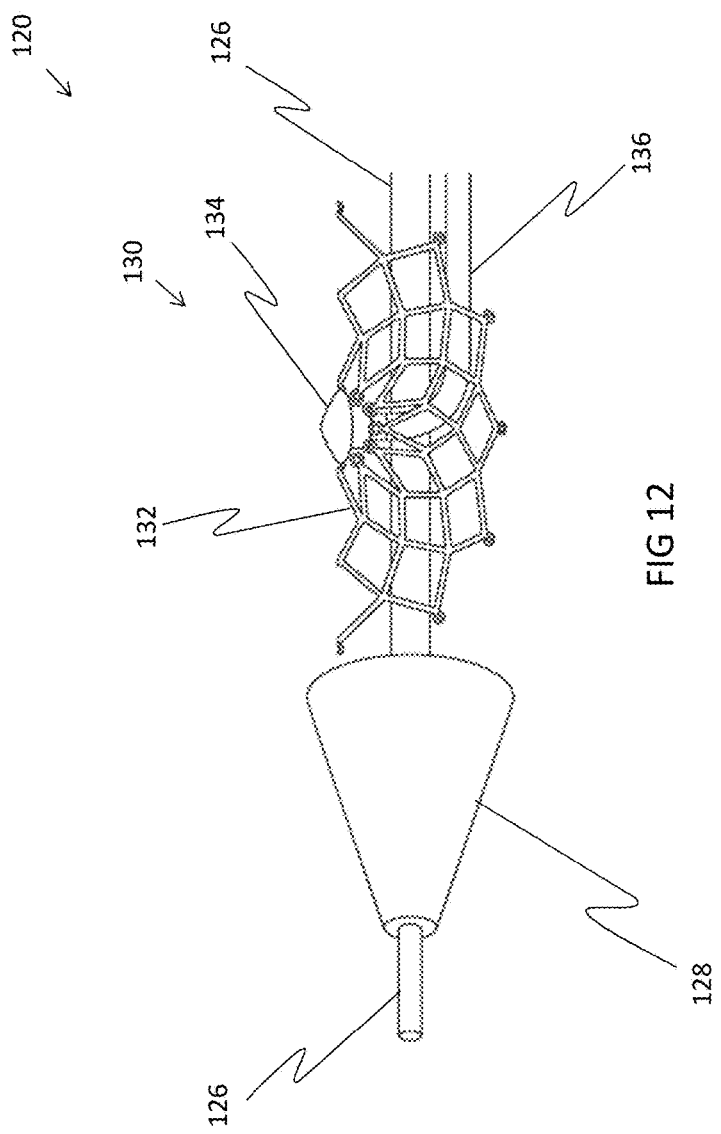

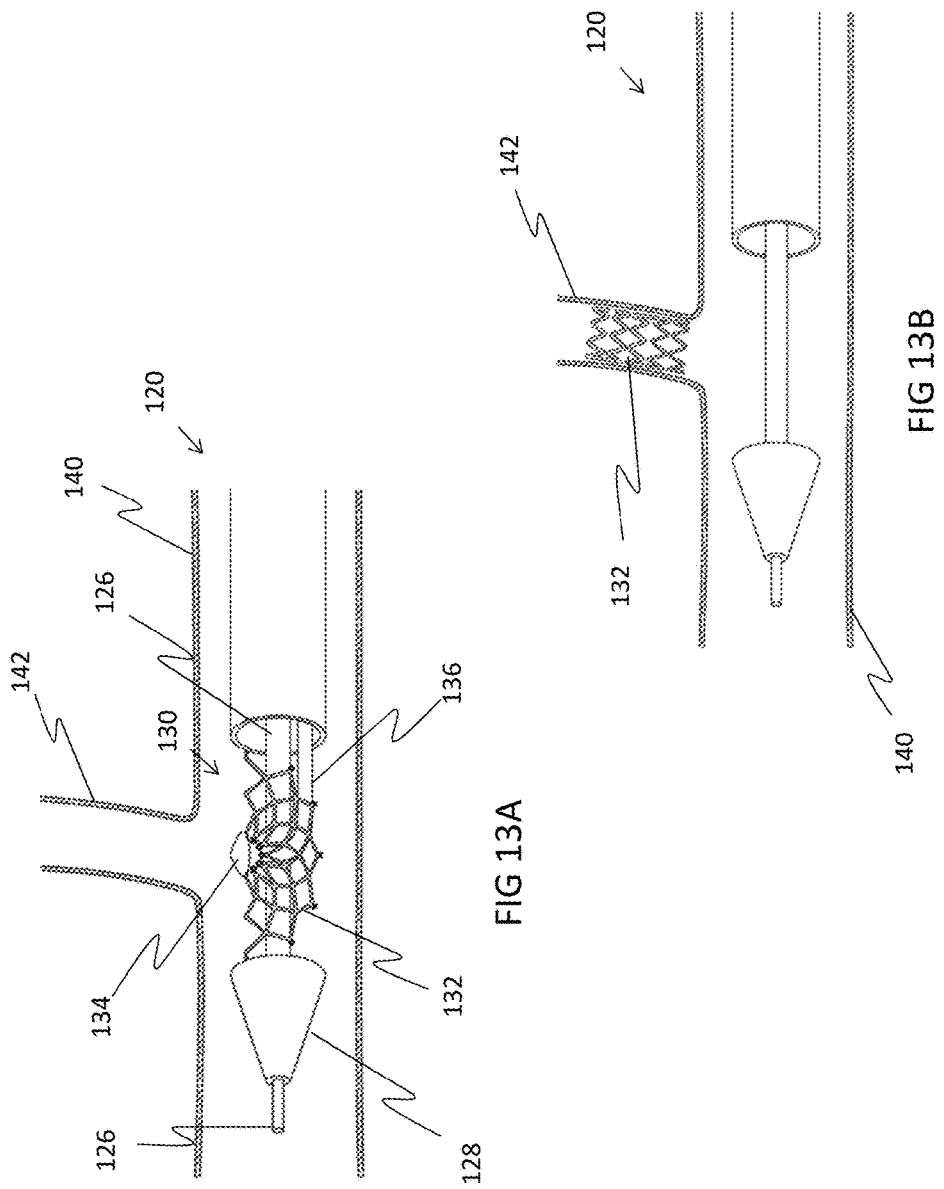

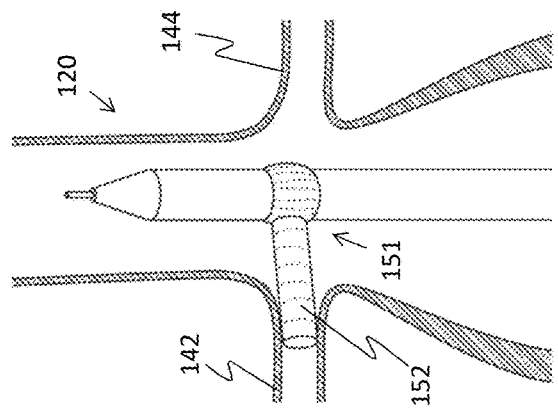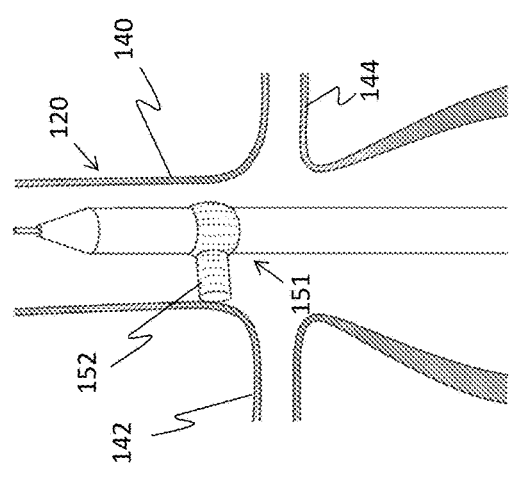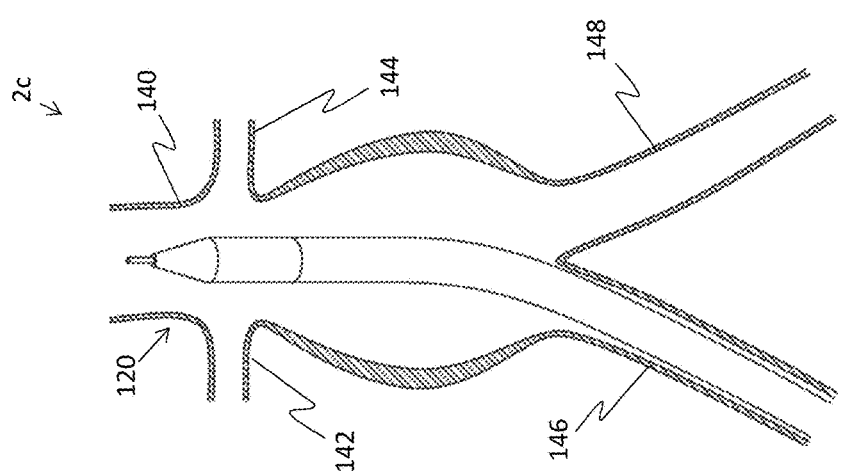

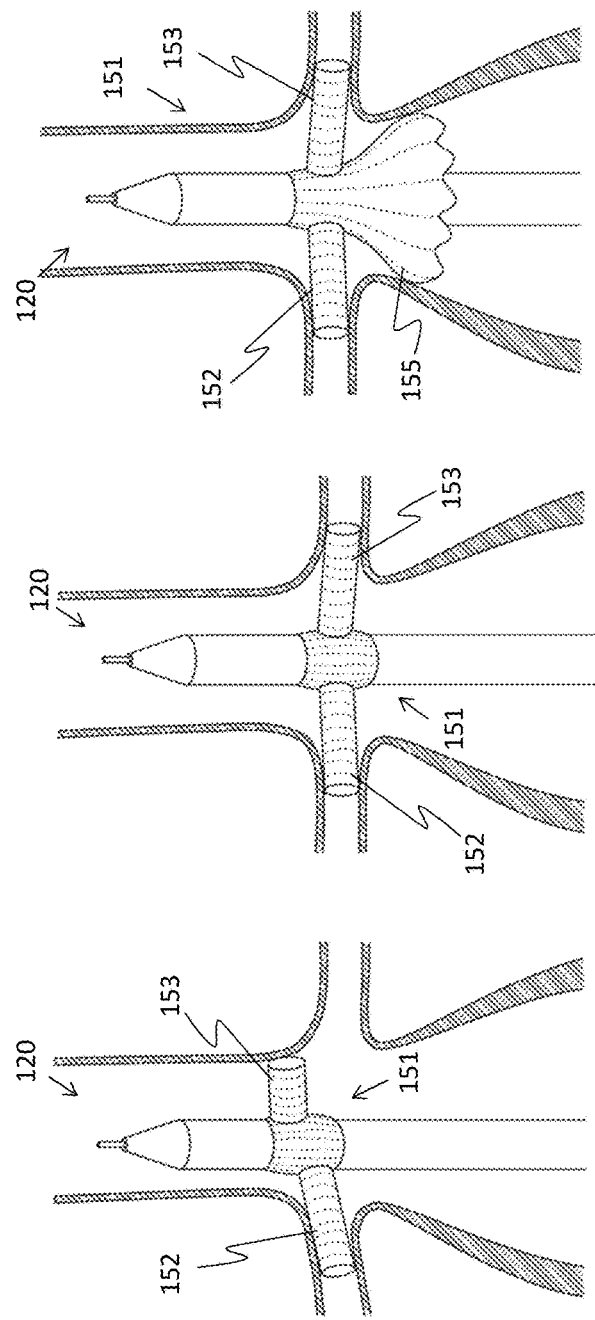

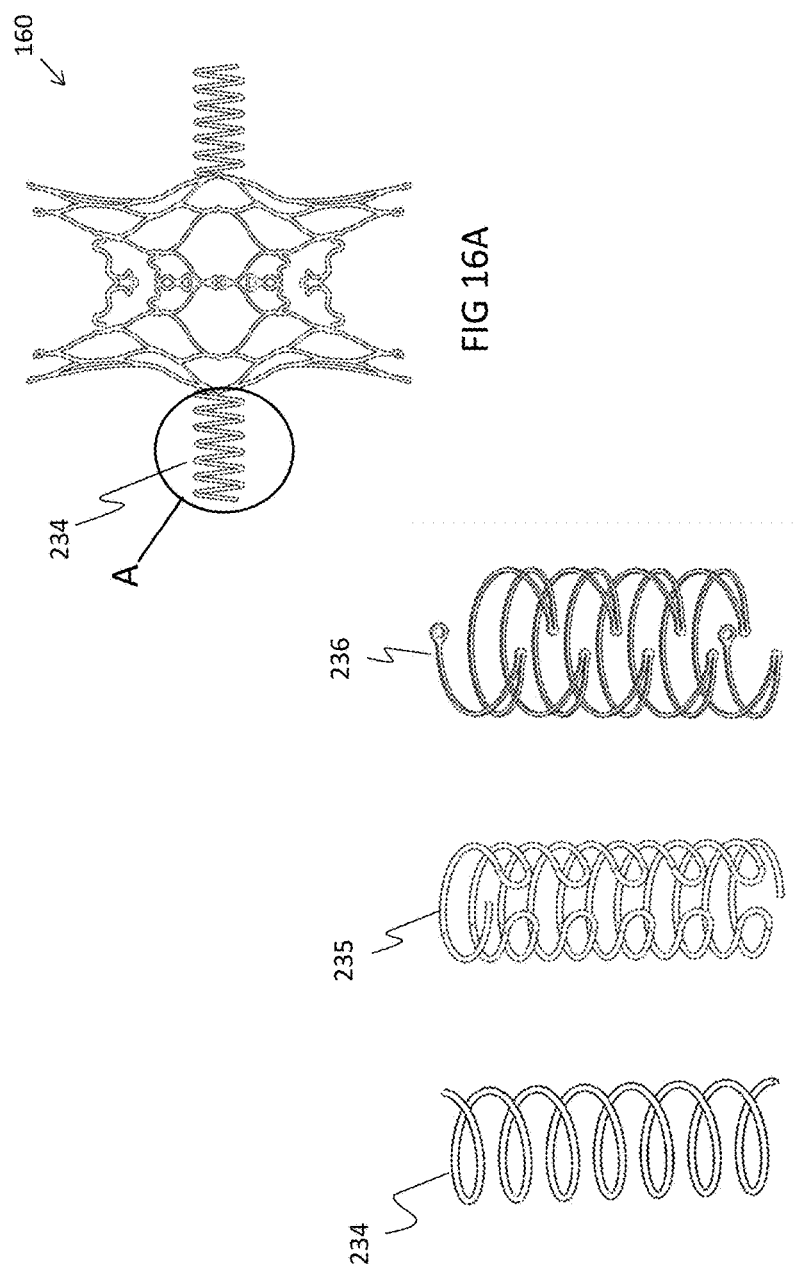

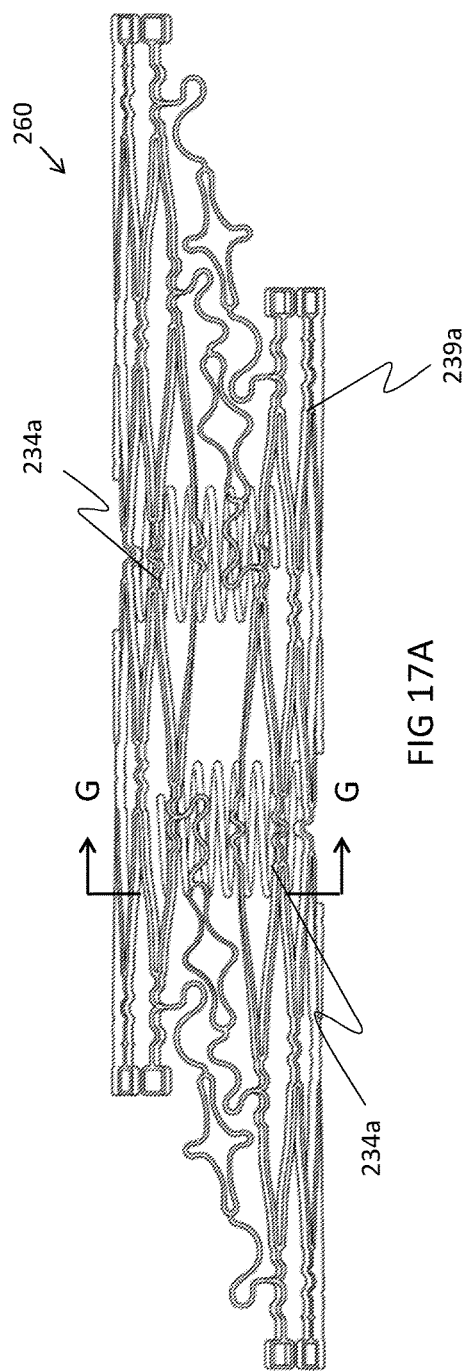
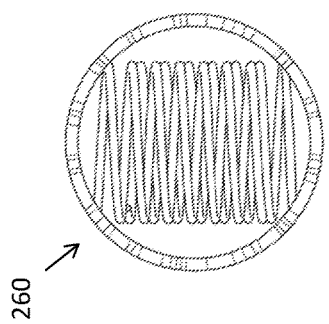
FIG 17A
FIG 17B
Section G-G

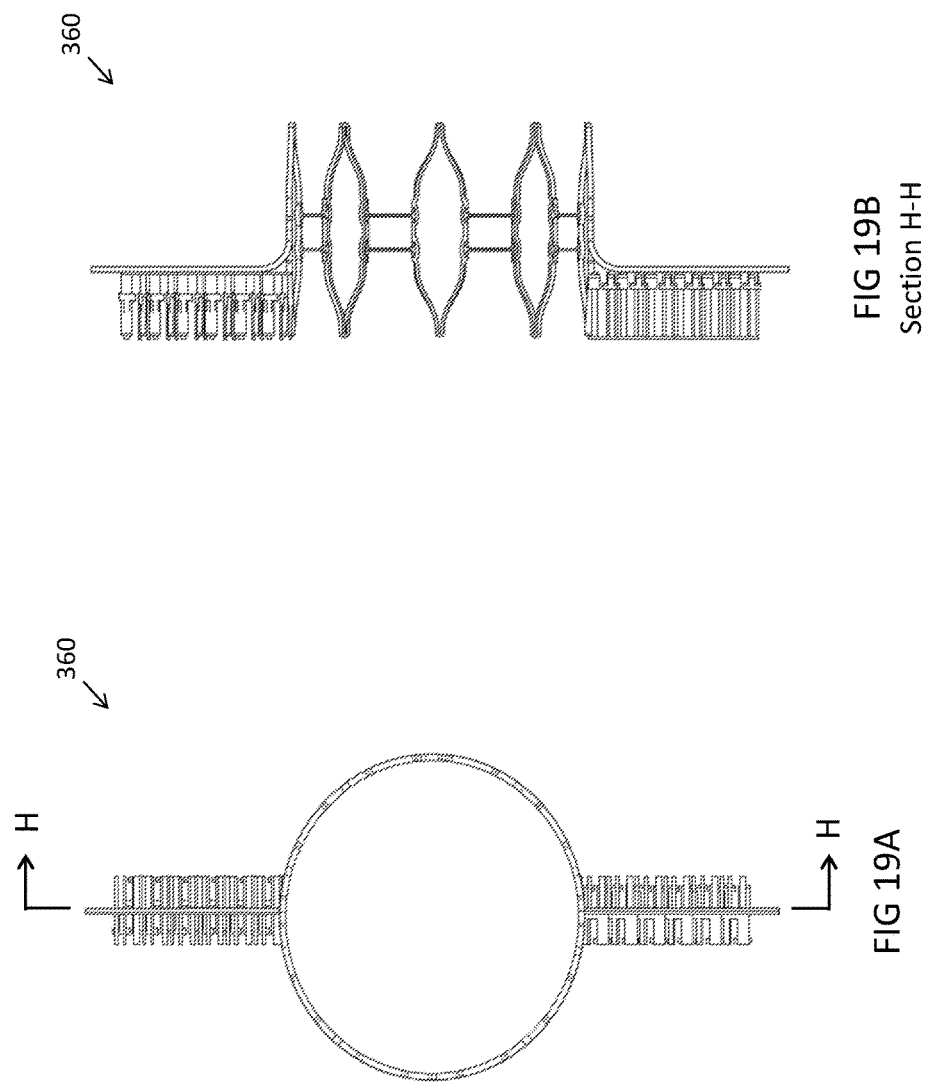

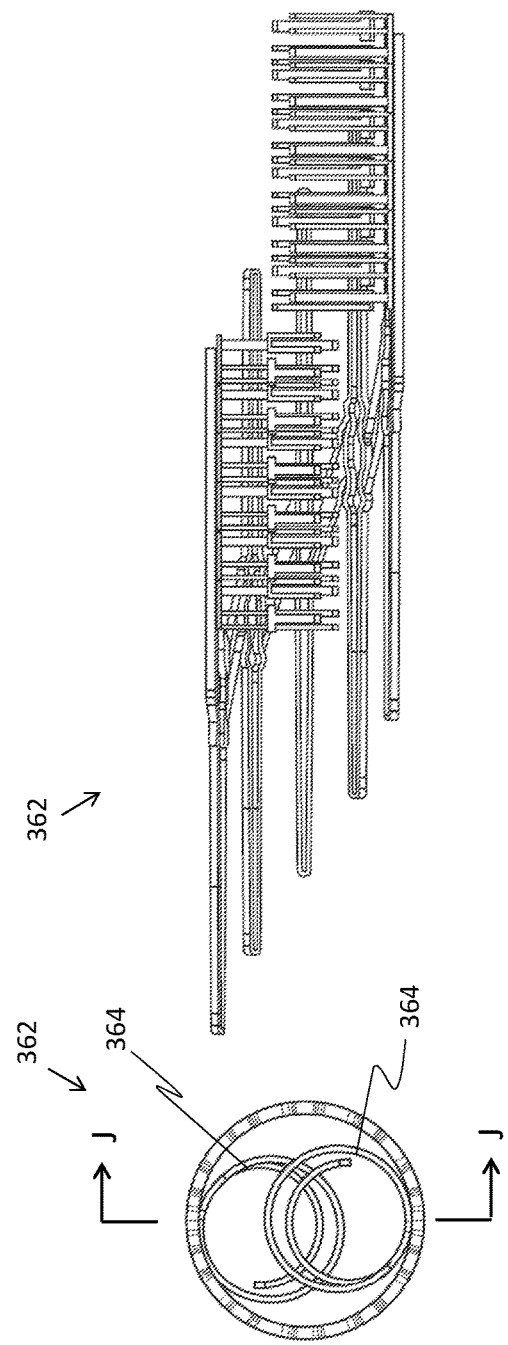

INTRAVASCULAR BIFURICATION ZONE IMPLANTS AND CRIMPING AND DEPLOYMENT METHODS THEREOF

The present application claims priority from U.S. Provisional Application No. 62/502,770, filed 8 May 2017, whose disclosure is incorporated herein by reference.

FIELD OF THE INVENTION AND BACKGROUND

The current invention relates to medical stents in general, and specifically to intravascular bifurcation zone implants and crimping and deployment methods thereof. In the specification and claims which follow hereinbelow, the term "implant" is a general term, interchangeable with "intravascular device"—both terms herein intended to mean "stent-graft"—as known in the art. The terms "bifurcation zone" and "bifurcation", and variations thereof, as used in the specification and claim which follow hereinbelow, are intended to mean points/places/zones in the vascular system where at least one secondary/side blood vessel branches out of a typically larger, main artery/blood vessel.

The term "delivery system", as used in the specification and claims which follow hereinbelow, is intended to mean a catheter and associated components, used to deliver and deploy an implant. Part of the catheter is a tube, as known in the art. The term "sheath", as used in the specification and claims which follow hereinbelow, is intended to mean a containment configuration/enclosure of one or more crimped stents. The sheath is included in the tube of the delivery system, as known in the art. Additional components of the delivery system include, but are not limited to: guide wires and other wire/activation mechanisms, typically included in the catheter. The catheter is characterized by a "distal end", meaning the end of the catheter inserted into the body to the proximity of the bifurcation zone, and a "proximal end", meaning the end of the catheter extending out of the body, from where the delivery system is activated/manipulated by a skilled individual. Typically, the sheath is located substantially at the distal end of the catheter.

The term "sub-procedure", as used in the specification and claims which follow hereinbelow is intended to mean an initial insertion of a delivery system into a body and/or a singular reinsertion of a delivery system or components thereof, typically following previous withdrawal of the delivery system from the body—all as part of an overall procedure or operation. As such, the term sub-procedure is intended to mean and include a singular insertion and associated withdrawal of the delivery system or components thereof.

The term "chronology", as used in the specification and claims which follow hereinbelow, in reference to an implant procedure, is intended to mean the overall time and/or sequence of sub-procedures involved in an implant procedure or operation. The duration and number of sub-procedures and/or their complexity contribute to longer chronology. Therefore, the term "chronology" is used interchangeably hereinbelow to additionally mean the sequence, relative complexity, and/or the number of sub-procedures involved in an implant procedure or operation. It is desirable to perform fewer and/or less time-consuming operations in a procedure—including the overall time and/or the number and/or sequence of operations. It is for this reason that shortening or lowering the chronology in an implant procedure is desirable.

A stent is placed or implanted within a vein, artery, or other tubular body organ, as known in the art, for treating an occlusion, stenosis, aneurysm, collapse, dissection, or weakened, diseased, or abnormally dilated vessel or vessel wall, inter alia, by expanding the vessel and/or by reinforcing the vessel wall. In particular, stents are quite commonly implanted into locations such as, but not limited to: coronary, cardiac, pulmonary, neurovascular, peripheral vascular, renal, gastrointestinal, and reproductive systems.

Two important currently-used applications for stents are directed to improving angioplasty results by preventing elastic recoil and remodeling of the vessel wall and for treating dissections in blood vessel walls caused by balloon angioplasty of coronary and peripheral arteries, by pressing together intimal flaps in the lumen at the site of a dissection. Conventional stents have been used with limited success rates for treating more complex vascular problems, such as lesions at or near bifurcation zones.

Conventional stent technology is relatively well-developed. Conventional stent designs typically feature a straight tubular-shape, single type cellular structure, configuration, or a pattern that is repetitive along the stent longitudinal axis. In many stent designs, the repeating structure, configuration, or pattern have strut and connecting-balloon catheter portions that can impede blood flow at bifurcations. In addition to various implant configurations addressing bifurcation stenting, there are many methods for delivering a stent at or near a bifurcation point, commonly called Fenestrated Endovascular Repair (FEVAR). The following are selected prior art addressing the problem.

Bourang, et al. in U.S. Pat. No. 9,737,424, whose disclosure is incorporated by reference, describe a crimping method that crimps a stent over multiple catheters. The method includes differentially crimping a stent on certain portions of a balloon catheter so that a second catheter can be threaded through the uncrimped portion of the stent and exit through the links of a conventional stent design or through a specific hole in the stent designed for a branched vessel.

In U.S. Pat. No. 9,730,821, whose disclosure is incorporated by reference, Bourang et al. describe a system for treating a bifurcation includes first and second delivery catheters, each having an expandable member. A stent having a side hole is disposed on the second delivery catheter. A portion of the first delivery catheter is disposed under a portion of the stent. The first delivery catheter is slidable relative to the second delivery catheter, and the first delivery catheter passes through the side hole. Expansion of the first expandable member expands a portion of the stent and expansion of the second expandable member expands the rest of the stent.

Pallazza, in U.S. Pat. No. 9,492,297, whose disclosure is incorporated by reference, describes an expandable medical balloon useful for treatment at a vessel bifurcation, the balloon having at least one expanded state, the balloon having at least one inner layer and at least one outer layer, the outer layer having at least one cavity therein through which the inner layer protrudes when the balloon is in its at least one expanded state, and methods of making and using the same.

In U.S. Pat. No. 9,610,182, whose disclosure is incorporated by reference, Douglas describes a system for treating disease involving branching vessels of a mammal system can include a main graft assembly (i) having a lumen permitting fluid flow therethrough, and (ii) configured to expand within a first vessel of a mammal; and a branch graft assembly including a branch cover (i) having a cover lumen permitting fluid flow therethrough; and (ii) configured to expand within a branch vessel that branches from the first vessel. The branch graft assembly may also include an expandable branch stent extending within the cover lumen. The branch graft assembly may further include a branch sheath (i) extending between the branch stent and the cover lumen, and (ii) constraining radial expansion of the branch stent within the cover lumen.

Feld et al., in U.S. Pat. No. 9,101,500, whose disclosure is incorporated by reference, describes methods and devices for placement of a stent in a bifurcation or ostial lesion. The stent comprises a main body and a flaring portion. The main body is designed to expand and support a main vessel of the bifurcation and defines a main body axis. The flaring portion is disposed on a side of the main body and is adapted to flare radially and offset the main body axis in response to expansion of the main body. The flaring portion comprises at least one distal wing and at least one proximal wing. Each wing is aligned along the main body axis. The at least one proximal wing is longer than the at least one distal wing, providing greater coverage of the proximal side of the side vessel than on the distal surface of the side vessel.

In U.S. Pat. No. 9,101,457, whose disclosure is incorporated by reference, Benary describes an endovascular stent-graft system, which includes fenestrated and crossing stent-grafts. The fenestrated stent-graft defines first and second lateral apertures in a central portion thereof, which apertures face in generally radially opposing directions. The crossing stent-graft includes one or more covering elements, which at least partially cover both end portions of the crossing stent-graft, such that a central portion is at least partially uncovered. Both stent-grafts are sized and shaped such that, when the crossing stent-graft is disposed through both apertures such that the central portion thereof is within the central portion of the fenestrated stent-graft, both end portions of the crossing stent-graft (a) pass through both apertures, respectively, and (b) when both stent-grafts are in radially-expanded states, form blood-impervious seals with both apertures, respectively.

Reference is currently made to FIG. 1A, which is a schematic view of a typical aortic renal zone having an endovascular aneurysm 3 and a prior art endovascular aneurysm repair (EVAR) implant 3. Prior art implant 3 is characterized by: a plurality of fixation of anchoring barbs 4; a main body 5; a contralateral gate 7; a contralateral limb extension 8; and an ipsilateral limb 9, in treatment of Abdominal Aortic Aneurysms (AAA)—all as known in the art Reference is additionally made to FIGS. 1B-1E, which are schematic diagrams of respective morphologies of Infrarenal (1B), Juxtarenal (1C), Pararenal (1D), and Suprarenal (1E) AAA—as known in the art—showing variations (2b, 2c, 2d, 2e) of typical aortic renal zone configuration 2 of FIG. 1A. An "aortic neck" (also referred to hereinbelow as "neck") is indicated by dimension "a", shown in FIGS. 1B and 1C. In prior art Juxtarenal/Suprarenal AAA repair, the presence of an aortic neck is necessary to receive fixation barbs 3 (ref FIG. 1A), which are used to anchor the implant onto the neck and to prevent a Type I endoleak. As such, the variations of typical aortic renal zone configuration corresponding to Juxtarenal, Pararenal, and Suprarenal AAA's are increasingly difficult/improbable choices for such repairs.

EVAR repair typically takes advantage of FEVAR, as known the art. Prior art FEVAR can be broadly described as employing one of two well-known implant types, namely: off-the-shelf implants and custom-made implants. In both cases, the fenestrated portion of a main stent refers to integrated "lateral fenestrated apertures": namely openings in a main stent, positioned to accommodate side-branching vessels and subsequent deployment and configuration of secondary (or "side") stents therein. Most typically, at least two smaller-diameter stents are deployed after passing through the lateral fenestrated apertures to fit secondary arteries, which branch out of the typically larger, main artery. These "smaller diameter portions" are also referred to herein below as "side stents"—as opposed to the "main stent". Representative steps in a typical FEVAR are presented hereinbelow.

Custom-made implants, as known in the art, which have heretofore been more prevalent for FEVAR, allow an optimal match to a specific bifurcation configuration and generally higher success rates. However custom-made implants have significant disadvantages such as, but not limited to: higher fabrication cost; and very long lead times to fabricate/fit the implant, as fabrication of custom-made implants involves time-consuming iterations between the manufacturer and physician, and the need for multiple CT scans of the patient—all additionally contributing to cost.

Off-the-shelf implants, on the other hand, generally address one or more "average" physiological bifurcation configurations—affording relatively lower fabrication cost and much quicker availability but not necessarily an optimal/custom fit—a point which is discussed further hereinbelow.

Some available off-the shelf implants, including the date of regulatory approval with CE mark for the European market, listed below according to EVAR and FEVAR, include:

EVAR
"Incraft", by Johnson & Johnson, 2014, 1820 McCarthy Blvd., Milpitas, Calif. 95035, USA
"Vanguard", by Boston Scientific, 2011, 300 Boston Scientific Way, Marlborough, Mass., 01752-1234, USA
"Excluder", by W. L. Gore & Associates, 2013, 555 Papermilll Rd., Newark, Del. 19711, USA
"Altura", by Lombard Medical, 2016, 4 Lombard Medical House, Trident Park, Didcot OX11 7HJ, UK
"Endurant II", Medtronic, 2016, 20 Lower Hatch Street,
"Netlix", 2013, and "Ovation", 2014, Endologix, 2 Musick, Irvine, Calif. 92618, USA
FEVAR
"Ventana™", ENDOLOGIX, INC., 2 Musick, Irvine, Calif. 92618 U.S.A.
"Zenith® p-Branch® Endovascular Graft", COOK MEDICAL LLC, P.O. Box 4195, Bloomington, Ind. 47402-4195, USA.
Some available FEVAR custom-made implants include:
"Anaconda™", Terumo Vaskutek, Newmains Avenue, Inchinnan, Renfrewshire, PA4 9RR, Scotland, UK
"Custom-made Zenith™", COOK MEDICAL LLC, P.O. Box 4195, Bloomington, Ind. 47402-4195, USA.

Limitations in Prior Art Implant Techniques

Prior art implant techniques in bifurcation zones are limited by catheter flexibility and rigidity, which subsequently impact the rigidity and length of a crimped implant device inside the sheath of the catheter.

Another limitation in prior art branch side stents or main stent frame extensions is that they typically address bifurcation inclinations of less than 70 degrees relative to the central axis of the main vessel. In cases where bifurcation inclinations exceed 70 degrees (ie approaching the normal, meaning 90 degrees) implant techniques become excessively complicated—as the catheter and its payload would be subject to relatively sharp bending. In addition to mechanical limitations imposed by crimping on prior art stents, inclusion of excessively-crimped prior art stents, combined with relatively sharp bending of the catheter can lead to mechanical fatigue/failure of the stent and thus pose excessive risk in such procedures and/or over time.

In the specification and claims hereinbelow, the expression "inclination of at least 70 degrees with respect to the main blood vessel longitudinal axis" is intended to mean an angle approaching the normal to the main blood vessel longitudinal axis, namely 90 degrees.

An example of a prior art related to crimping of stents is Kheradvar et al., in U.S. Pat. No. 8,702,788, whose disclosure is incorporated by reference, describes an expandable stent that can transform between a collapsed state and an expanded state. The stent includes a first cross-sectional shape and a second cross-sectional shape. The first cross-sectional shape is a non-convex shape when the stent is in the collapsed state. Alternatively, the second cross-sectional shape is a convex shape when the stent is in an expanded state. The stent can be formed of super elastic Nitinol, which allows it to be shape set in the desired shape. Due to its shape setting properties and the non-convex cross-section, the stent is capable of dramatically reducing its cross-sectional radial profile which is beneficial in a variety of procedures.

In addition to the limitations noted above, when the implant is deployed (including the side stent) the overall, final implant configuration can be exposed to material fatigue, as the bifurcation angle predisposes the side stent to strut fracture. Additionally, any open areas between the main stent and the side stent following balloon dilatation can lead to thrombus and/or endoleaks, as known in the art.

A more complicated case presents itself when the ratio of the main vessel diameter to the secondary vessel diameter is greater than 2. In such a configuration, deployment of a side stent is typically more complicated, for reasons as noted hereinabove.

In other scenarios, such as in the carotid artery, in the Willis region (also known as "Circle of Willis"), blood flow must not be blocked during deployment of the implant from the catheter, as the organ fed by the secondary vessel (in this case, the brain) must receive blood during the procedure to maintain organ functionality. In renal artery-related procedures, blood flow may be temporarily limited, but only for short periods.

Implant producers are faced with formidable challenges to support all sizes/scales of vessels having variable amorphic geometries, varying from patient-to-patient—all in addition to addressing parameter changes, as discussed further hereinbelow.

Aortic renal zones represent an exemplary case of multi-parameter geometry varying among patients—including: scale variations of different diameters for the main aorta vessel and renal branch vessels; height differences between left and right renal arteries; and angular variations between renal vessels relative to the axis of the aorta in both radial and axial directions.

Representative Steps in a FEVAR Procedure

Representative steps in a FEVAR procedure using implants such as those indicated hereinabove are described by S. Oderich et al. in "Technical Aspects of Repair of Juxtarenal Abdominal Aortic Aneurysms using the Zenith Fenestrated Endovascular Atent Graft", Journal of Vascular Surgery 2014; 59:1456-61, whose disclosure is incorporated by reference. Reference is currently made to FIGS. 2-6, which are schematic cross-sectional views of a typical aortic renal zone 10, showing a main artery 11 and steps in a Prior Art FEVAR procedure (suprarenal components only), as described by Oderich et al.

Current FEVAR and similar endovascular repair procedures are characterized by the following summarized steps:

1. Precathetization of target vessels 12 (ie renal arteries) is performed, passing guide wires 14 to the so-called "landing location". The delivery system addresses complex vessel turns in typically narrow blood vessel channels—ref FIG. 2.
2. In FIG. 3, a catheter 20, including a crimped stent 21, is inserted. Stent fenestrations 22 are then aligned with the target vessels, by rotating the catheter, as indicated by the arrows. Typically, orientation of fenestrations 22 with regard to the guide wires is ascertained using imaging techniques. (Duplicate indicia, as indicated in FIG. 2, are not indicated in the current and following figures for purposes of clarity.)
3. Guide wires 14 are removed/withdrawn and then reintroduced, this time gaining accesses from within the fenestrated stent—ref FIG. 4.
4. In FIG. 5, stent 21 is deployed, including proximal balloon dilatation of the suprenal stent graft (ie stent 21) and catheter 20 (ie delivery system) is removed/withdrawn.
5. Balloon-expandable stents 25 are deployed into renal arteries 12, with proximal flaring of respective stents 25 performed with angioplasty ballooning.

Additional Limitations and Risks in Prior Art Implant Techniques

The multi-parameter geometry as described hereinabove calls for a corresponding multi-parameter solution. One solution known in the art is based upon multi-component implantation of an independent/main implant (for aorta and renal applications), which is subsequently connected by shrink fitting (stent-within-stent) to one or more branch stents after deployment—such as described by Oderich et al., hereinabove. Connection of the stent components takes place in an amorphic, native vessel geometry, which is influenced by regular, pulsating blood flow. Such a multi-component solution demands production of a dedicated delivery system for each component and a relatively long-chronology transcatheter surgery procedure. As noted in the description of FIGS. 2-6 hereinabove, such a transcatheter procedure requires multiple vessel entrances to allow ingress for guidewires and support equipment. In the case of the risk of aorta rupture based on the para-renal aneurysm, the multi-component transcatheter procedure described hereinabove may provide a solution, albeit a complicated one. Among the factors adding to risk from/following the procedure are:

- migration of the stent-graft and side stents;
- renal events (such as: renal artery stenosis, occlusions, and infarcts);
- post-operative acute renal failure (ARF);
- fatigue and fracture of the stent/stents;
- ischemic strokes, in case of the complicated renal arteries angularity, and required manipulation of brachiocephalic vessels during side stent implantation; and
- endoleaks following the procedure.

Some factors adding to complexity in a procedure are:

- long procedure time—ie long chronology—with a typical total operation time between 2 to 3 hours and fluoroscopy time between 50-70 minutes;
- involvement of support equipment for a FEVAR procedure (such as: a multi-sheath introducer, a marker catheter, and dedicated post dilatation balloons); and multiple renal artery approaches for complex angularity cases (such as through brachiocephalic and left subclavian arteries) with accompanying increased risk of an ischemic stroke.

In addition to the risk and complexity elements noted hereinabove, the variation of different products from different vendors and of the deployment and fixation of each component in a procedure can contribute to unpredictability of functionality of a complete implant—again exacerbating overall cost and/or risk.

As observed in the procedures outlined above, off-the-shelf implants have integrated lateral fenestrated apertures not necessarily custom-fit to the patient. This constraint imposes a major impact on the chronology of the procedures—as repetitive sub-procedures and most careful attention must be given to attempt to align the lateral fenestrated apertures of the stent with a given patient morphology. There are a number of documented risks associated with off-the-shelf implants and deployment methods following Juxtarenal/Suprarenal AAAs Repair, as a part of FEVAR procedure, as presented hereinbelow:

A. Kitagawa et al., in an article entitled: "Zenith p-branch Standard Fenestrated Endovascular Graft for Juxtarenal Abdominal Aortic Aneurysms", Society for Vascular Surgery, 2013—whose disclosure is incorporated by reference—indicates that the overall applicability of stent-graft was 72% for patient aneurysms. There is no description of success rate (usually relating to results of the procedure) as the article does not deal with any procedure results, but rather applicability of the stent graft.

R. K. Greenberg et al., in an article entitled: "Intermediate Results of a United States Multicenter Trial of Fenestrated Endograft Repair For Juxtarenal Abdominal Aortic Aneurysms", J Vasc Surg for FEVAR, 2009, whose disclosure is incorporated by reference, notes that after FEVAR, based on the intermediate-term (24-month) results, up to 30% of the patients experienced a renal event (renal artery stenoses, occlusions, and infarcts).

In an article entitled: "Durability Of Branches In Branched And Fenestrated Endografts", by T. M. Mastracci et al., 2013, J Vasc Surg, whose disclosure is incorporated by reference, it is indicated that based on the long-term clinical follow up, the maximal cause for reinterventions is caused by failure in the renal arteries (6% of right renal artery and 5% of left renal artery).

A final example is by T. Martin-Gonzalez et al., in an article entitled: "Renal Outcomes Following Fenestrated and Branched Endografting", Eur J Vasc Endovasc Surg, 2015, whose disclosure is incorporated by reference. T. Martin-Gonzalez et al note that post-operative acute renal failure (ARF) was seen in 29% of patients with median follow up 3.1 years (2.9-3.3 years).

As such, it may be summarized that current prior art implant procedures have risks, complexity, and expenses, along with concomitant long procedural chronologies.

There is therefore a need for implant configurations and associated techniques that can allow additional/more effective crimping of stents to address aorta and bifurcation branches using a singular procedure and/or minimal sub-procedures, thereby yielding minimal and/or reduced chronology and having concomitant higher success rates (and/or lower risks) in the short and long run. Such implants and techniques would be especially beneficial for endovascular Juxtarenal, Pararenal, and Suprarenal Abdominal Aortic Aneurysm (AAA) and analogous Thoracic Aortic Aneurysm (TAA) procedures/repairs.

SUMMARY OF INVENTION

According to the teachings of the current invention, there is provided a multi stent delivery system for intravascular bifurcation zone delivery and deployment of a multi stent, the bifurcation zone having a main blood vessel, the main blood vessel having a main blood vessel longitudinal axis and at least one side blood vessel inclined/branching out of the main blood vessel, the delivery system comprising: a catheter having a catheter longitudinal axis substantially coaxial with the main blood vessel longitudinal axis, a tube positioned coaxially within the catheter, the catheter having a distal end and a proximal end, and the tube containing: at least one crimped side stent for deployment substantially normal to the catheter longitudinal axis and into the side blood vessel; and at least one crimped main stent for deployment substantially along the catheter longitudinal axis into the main blood vessel; wherein the at least one crimped side stent and at least one crimped main stent are part of a unified/singular configuration within a sheath, located substantially at the distal end.

Preferably, the at least one crimped side stent and the at least one crimped main stent have respective configurations characterized by a substantially flattened, curved shape, and having an overlapping geometry, the crimped stents having a reduced cross-section within the sheath. Most preferably, the at least one side stent is deployed in the at least one side blood vessel having an inclination of at least 70 degrees with respect to the main blood vessel longitudinal axis. Typically, the multi stent is deployed in the main blood vessel and the at least one side blood vessel, the main blood vessel and the at least on side blood vessel having respective diameters, and a ratio of the respective diameters is at least 2. Most typically, delivery and deployment of the multi stent multi stent is part of an endovascular aneurysm repair (EVAR) procedure and wherein the bifurcation zone includes a Juxtarenal Abdominal Aortic Aneurysm (AAA). Preferably, delivery and deployment of the multi stent multi stent is part of an endovascular aneurysm repair (EVAR) procedure and wherein the bifurcation zone includes at least one aneurysm chosen from the group including: Pararenal AAA and Suprarenal AAA. Most preferably, the delivery and deployment of the multi stent multi stent is a sub-procedure of the EVAR procedure, the sub-procedure including a singular insertion and associated withdrawal of the delivery system or components thereof, thereby serving to reduce a chronology of the procedure.

According to the teachings of the current invention, there is further provided a method of delivering and deploying a multi stent using a multi stent delivery system for an intravascular bifurcation zone, the bifurcation zone having a main blood vessel with a main blood vessel longitudinal axis and at least on side blood vessel inclined/branching out of the main blood vessel, wherein the bifurcation zone has at least on side blood vessel branching out of a main blood vessel, the method including the steps of: taking a catheter having a catheter longitudinal axis substantially coaxial with the main blood vessel longitudinal axis, and having a tube coaxially-positioned within the catheter, the catheter having a distal end and a proximal end; crimping the at least one side stent and at least one main stent to form a unified/singular configuration within a sheath, the sheath located substantially at the distal end; deploying the at least one crimped side stent substantially normal to the catheter longitudinal axis and expanding the side stent into the side blood vessel; and deploying the at least one crimped main stent substantially along the catheter longitudinal axis and expanding the at least one main stent into the main blood vessel. Preferably, the at least one crimped side stent and the at least one crimped main stent have respective configurations characterized by a substantially flattened, curved shape, and having an overlapping geometry, the crimped stents having a reduced cross-section within the sheath. Most preferably, the at least one side stent is deployed in the at least one side blood vessel having an inclination of at least 70 degrees with respect to the main blood vessel longitudinal axis. Typically, the multi stent is deployed in the main blood vessel and the at least one side blood vessel, the main blood vessel and the at least on side blood vessel having respective diameters, and a ratio of the respective diameters is at least 2. Most typically, delivery and deployment of the multi stent is part of an endovascular aneurysm repair (EVAR) procedure and wherein the bifurcation zone includes a Juxtarenal Abdominal Aortic Aneurysm (AAA). Preferably, delivery and deployment of the multi stent is part of an endovascular aneurysm repair (EVAR) procedure and wherein the bifurcation zone includes at least one aneurysm chosen from the group including: Pararenal AAA and Suprarenal AAA. Most preferably, the multi stent is delivered and deployed as one sub-procedure of the EVAR procedure, the sub-procedure including a singular insertion and associated withdrawal of the delivery system or components thereof, thereby serving to reduce a chronology of the procedure.

According to the teachings of the current invention, there is further provided a method of delivering and deploying a multi stent comprising a main stent, a first side stent and a second side stent, using a multi stent delivery system for an intravascular bifurcation zone and delivering and deploying the multi stent, as part of an endovascular aneurysm repair (EVAR) procedure, the bifurcation zone including a main blood vessel and a first and a second side blood vessel, and the bifurcation zone further including at least one aneurysm chosen from the group including: Juxtarenal Abdominal Aortic Aneurysm (AAA), Pararenal AAA and Suprarenal AAA, whereby delivering and deploying the multi stent is performed as one sub-procedure of the EVAR procedure, the sub-procedure including a singular insertion and associated withdrawal of the delivery system or components thereof, the method including the steps of: translating and rotating a catheter, the catheter being part of the multi stent delivery system and having a catheter longitudinal axis, within the main blood vessel and rotating the catheter within the main blood vessel to position the multi-stent delivery system across from the first side blood vessel; partially deploying the first side stent substantially perpendicularly from the catheter longitudinal axis in the direction of the first side blood vessel; rotating/steering the partially-deployed first side stent to align the first side stent substantially concentrically with the first side blood vessel; fully deploying the first side stent into the first side blood vessel, repeating steps a-c to complete a full deployment of the first side stent into the first side vessel; translating and rotating the catheter, to position the multi-stent delivery system across from the second side blood vessel; partially deploying the second side stent substantially perpendicularly from the catheter longitudinal axis in the direction of the second side blood vessel; rotating/steering the partially-deployed second side stent to align the second side stent substantially concentrically with the second side blood vessel; fully deploying the second side stent into the second side blood vessel, repeating steps e-g to complete a full deployment of the second side stent into the first side vessel; deploying the main stent into the main blood vessel along the catheter longitudinal axis, the main stent having lateral respective fenestrations corresponding to the first and second blood vessels and with previously-deployed side stents secured in the respective fenestrations thereby securing the multi stent in the bifurcation zone; withdrawing the catheter; and deploying an implant in a separate sub-procedure, and applying fixation barbs to secure the implant directly to the multi-stent configuration— and not to the main blood vessel.

LIST OF FIGURES

The invention is herein described, by way of example only, with reference to the accompanying drawings, wherein:

FIGS. 1B-1E are schematic diagrams of respective morphologies of Infrarenal (1B), Juxtarenal (1C), Pararenal (1D), and Suprarenal (1E) AAA—as known in the art— showing variations (2b, 2c, 2d, 2e) of the typical aortic renal zone configuration of FIG. 1A;

FIGS. 7A-7D are a series of top and side views of an initial/deployed stent configuration (FIGS. 7A and 7B) and of crimped stent configuration (FIGS. 7C and 7D), in accordance with embodiments of the current invention;

FIGS. 8A-8G are a series of top and side views of an initial/deployed stent configuration (FIGS. 8A and 8B), of an intermediate crimped stent configuration (FIGS. 8C and 8D), and of a final crimped stent configuration (FIGS. 8E, 8F, and 8G), in accordance with embodiments of the current invention;

FIGS. 9A-9C are a side view of an initial/deployed stent configuration (FIG. 9A) and top and side views of crimped stent configuration (FIGS. 9B and 9C), in accordance with embodiments of the current invention;

FIGS. 10A-10C are a side view of an initial/deployed multi-stent configuration (FIG. 10A) and top and side views of crimped multi-stent configuration (FIGS. 10B and 10C), in accordance with embodiments of the current invention.

FIG. 11A is a cross-sectional view of the Prior Art catheter and stent, shown previously in FIGS. 3 and 4;

FIGS. 11B-11E are cross-sectional views of catheters having crimped stents configured therein, in accordance with embodiments of the current invention;

Figure 14B:
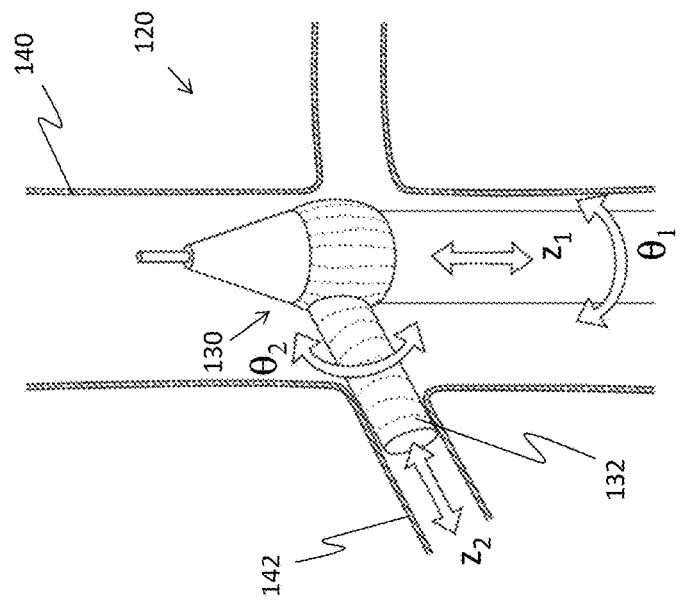
Figure 14A:
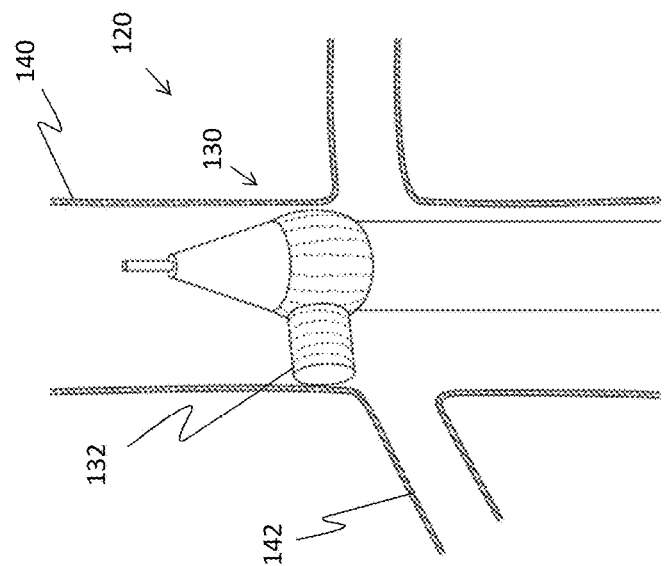
Figure 18A:
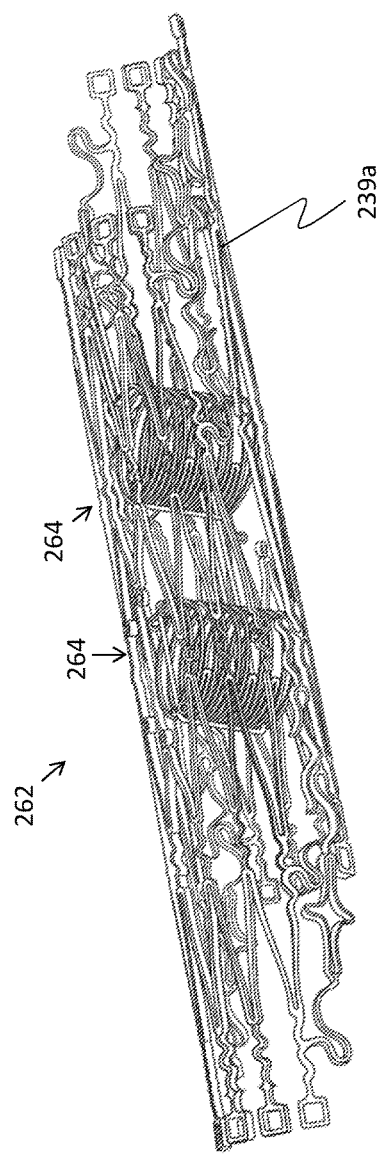
Figure 18B:
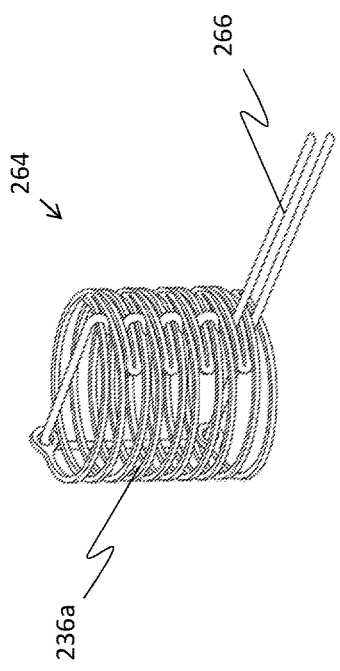

FIG. 12 a schematic side view of the catheter shown in FIG. 11B (with catheter tube removed for purposes of illustration), in accordance with embodiments of the current invention;

FIGS. 13A and 13B are schematic views of the catheter shown in FIG. 12, further indicating a main blood vessel and a side blood vessel, having a larger than 70-degree orientation to the main blood vessel, in accordance with embodiments of the current invention;

FIGS. 14A and 14B are schematic views of the catheter shown in FIGS. 12 and 13, showing deployment of the side stent into the side blood vessel, in accordance with embodiments of the current invention;

FIGS. 15A-15H are schematic cross-sectional representations of the aortic renal zone and the Juxtarenal Abdominal Aortic Aneurysm (AAA) shown hereinabove in FIG. 1C, with the current figures showing the sequence of steps for implant delivery in EVAR, in accordance with embodiments of the current invention;

FIGS. 16A and 16B are a side isometric view of a deployed multi-stent configuration (similar to the multi-stent configuration shown in FIG. 10A) and isometric representations of three exemplary side stent configurations, in accordance with embodiments of the current invention;

FIGS. 17A and 17B are schematic side and cross-sectional representations of a crimped multi-stent configuration, having a crimped main-stent configuration similar to the crimped main-stent configuration shown in FIG. 10C, in accordance with embodiments of the current invention;

FIGS. 18A and 18B are isometric views of a crimped multi-stent configuration, similar to the crimped multi-stent configuration shown in FIGS. 17A and 17B, and controlled side stent deployment systems in accordance with embodiments of the current invention; and FIGS. 19A-19D are schematic and sectional views of an initial-shape/deployed alternate multi-stent configuration and a crimped alternate multi-stent configuration, in accordance with embodiments of the current invention.

DETAILED DESCRIPTION

Embodiments of the present invention relate to intravascular bifurcation zone implants and crimping and deployment methods thereof. Furthermore, embodiments of the current invention are applicable to deployment of an implant for bifurcation inclinations greater than 70 degrees relative to the central axis of the main vessel (ie approaching the normal, meaning 90 degrees) and/or when the ratio of the main vessel diameter to at least one secondary vessel diameter is greater than 2.

Embodiments of the current invention provide for novel crimping and deployment techniques for bifurcation stents and temporary embolic protection devices as part of the complex scaffolding that includes a main vessel device which supports branch components/side stents for passive and active functional use.

Embodiments of the current invention include stent configurations and crimping processes thereof which enable transforming an initial/deployed cylindrical shape of a stent to a crimped, curved and/or substantially flattened shape. The curvature of the crimped stent serves to define a sheath diameter and an inner diameter of the catheter/delivery system in most cases yielding reduced diameters and/or higher utilization of space within the catheter inner diameter, as described further hereinbelow.

Figure 8G:
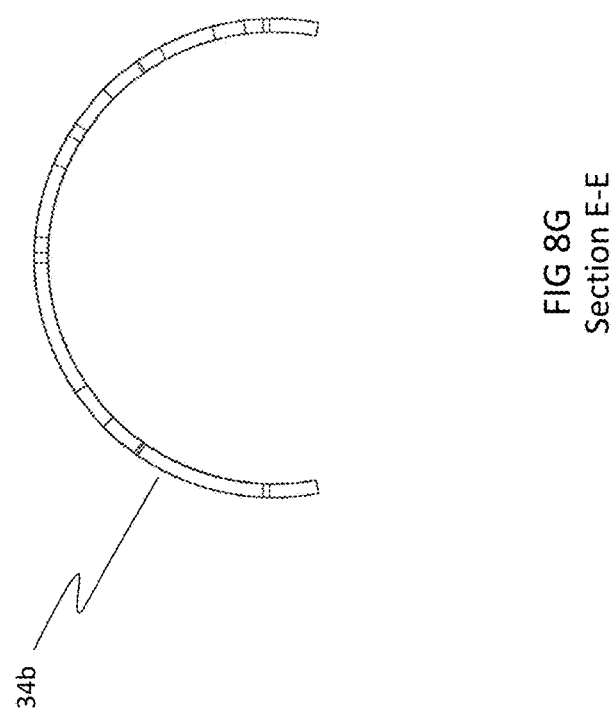

Reference is currently made to FIGS. 7A-7D, FIGS. 8A-8G, and FIGS. 9A-9C, which are a series of top and side views of exemplary initial/deployed and crimped stent/stent configurations, additionally referred to as "side stents" and/or "secondary stents", in accordance with embodiments of the current invention. Specifically: FIGS. 7A-7D are a series of top and side views of an initial/deployed stent configuration 30 (FIGS. 7A and 7B) and of crimped stent configuration 30a (FIGS. 7C and 7D); FIGS. 8A-7G are a series of top and side views of an initial/deployed stent configuration 34 (FIGS. 8A and 8B), of an intermediate crimped stent configuration 34a (FIGS. 8C and 8D), and of a final crimped stent configuration 34b (FIGS. 8E, 8F, and 8G); and FIGS. 9A-9C are a side view of an initial/deployed stent configuration 36 (FIG. 9A) and top and side views of crimped stent configuration 36a (FIGS. 9B and 9C), all in accordance with embodiments of the current invention.

Common to all the exemplary secondary stents/stent configurations shown in FIGS. 7A-7D, FIGS. 8A-8G, and FIGS. 9A-9C are the following:

unique configuration/construction, allowing compact crimping to a substantially flattened, curved shape without excessive mechanical stress/strain on the stent, to present a significantly reduced cross-section within a sheath and within a delivery system—as detailed further hereinbelow;

self-expansion—meaning, once the crimped stent is deployed from the delivery system the stent can open on its own; without the need for a balloon and/or other deployment mechanism; and controlled expansion—meaning the deployed stent, in addition to being self-expanding is nonetheless controlled as it expands—as detailed further hereinbelow;

construction from metallic (such as smart memory alloys) and/or plastic materials, as known in the art; and may be incorporated with a main, larger stent (as described further hereinbelow), thereby allowing deployment of one or more secondary stents, along with the main stent, thereby yielding a reduced procedure chronology—as detailed further hereinbelow.

Figure 10A:
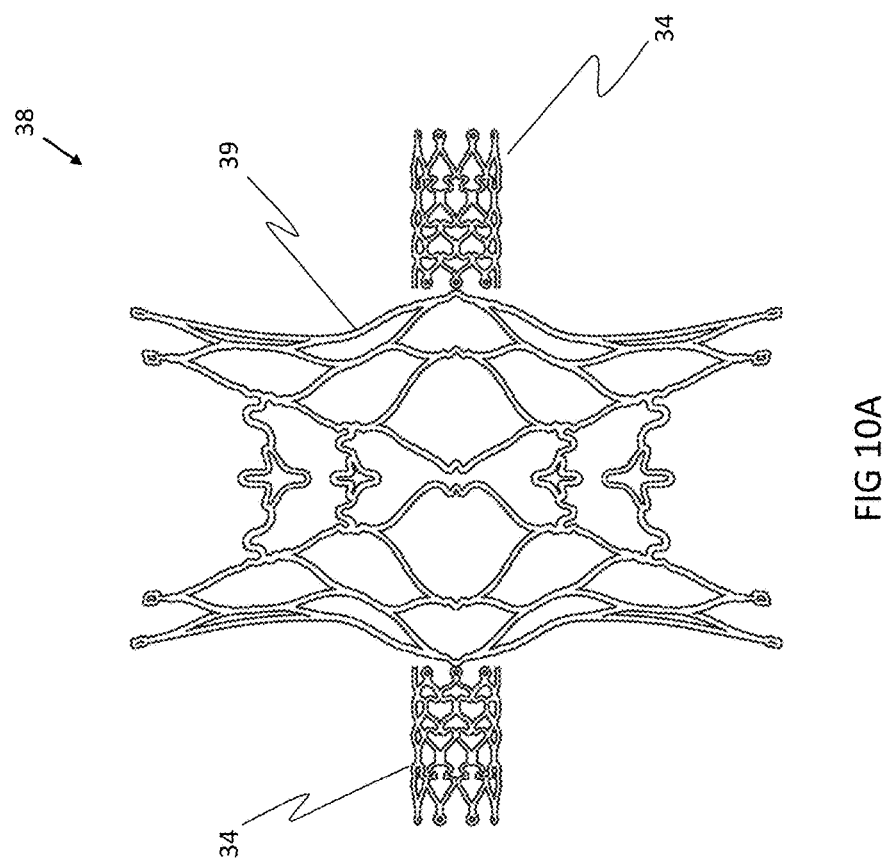

Reference is currently made to FIGS. 10A-10C, which are a side view of an initial/deployed multi-stent configuration 38 (FIG. 10A) and top and side views of crimped multi-stent configuration 38a (FIGS. 10B and 10C), all in accordance with embodiments of the current invention. Multi-stent configurations 38 and 38a further include respective deployed and crimped main stent configurations 39 and 39a and respective deployed and crimped secondary stent configurations 34 and 34b (as shown in FIGS. 8A-8G). Whereas respective deployed and crimped side stent configurations 34 and 34b are included as side stents in multi-stent configurations 38 and 38a, any of the exemplary deployed and crimped secondary stent configurations presented hereinabove in FIGS. 7A-7D (ie side stents 30 and 30a), or FIGS. 9A-9C (ie 36 and 36a) or any secondary stents having a similar configuration—may likewise be used/substituted as side stents.

As noted previously, the configuration/construction of the exemplary stents introduced hereinabove, all having deformable elements as shown in the figures, enables crimping the respective stents to a curved, substantially flat shape and/or inclusion in the sheath having a significantly reduced cross-section within a sheath and a delivery system. The curvature/periphery of the exemplary crimped stent serves to define a sheath diameter (and thus an inner diameter of the catheter/delivery system)—in many cases having a reduced catheter diameter and/or higher utilization of space within the catheter inner diameter, as described further hereinbelow.

Figure 3:
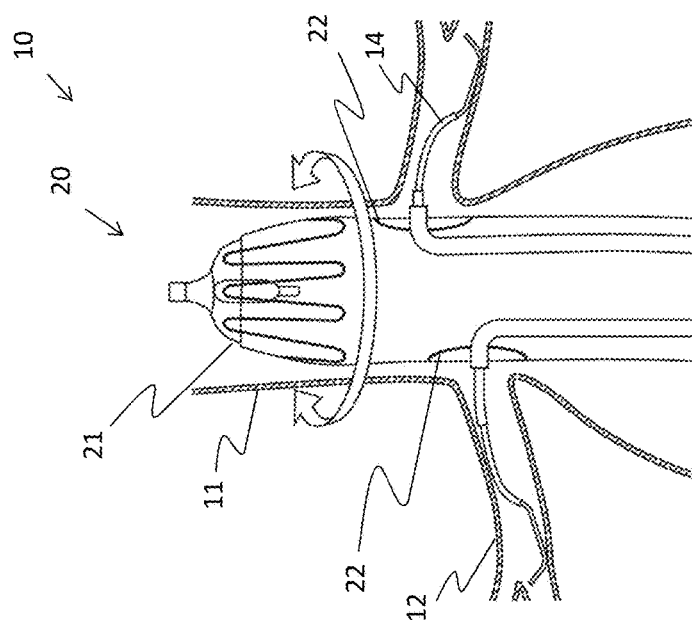
FIGS. 2-6 are schematic cross-sectional views of a typical aortic renal zone, showing a main artery and steps in a Prior Art FEVAR procedure (suprarenal components only), as described by Oderich et al.
Figure 2:
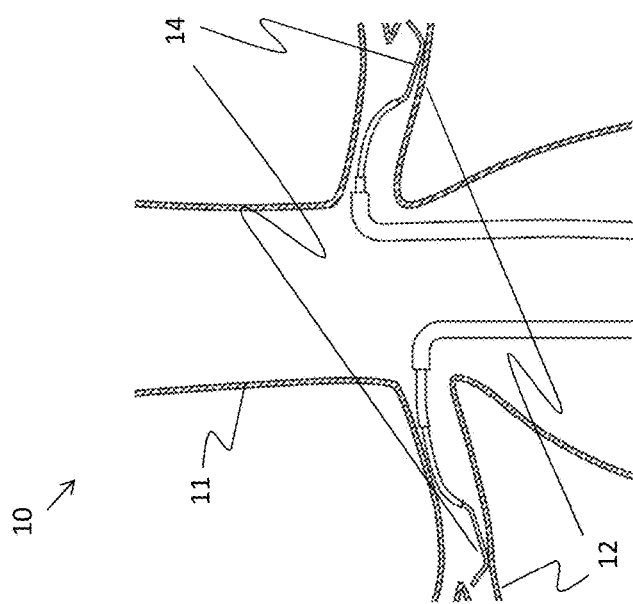
Figure 5:
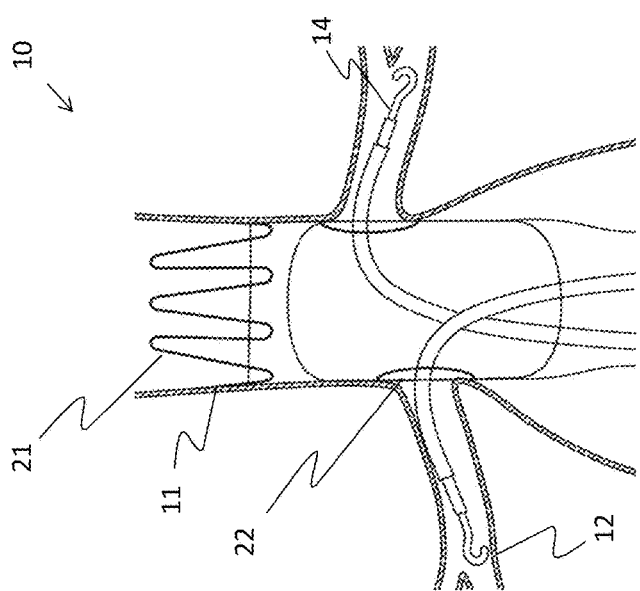
Figure 4:
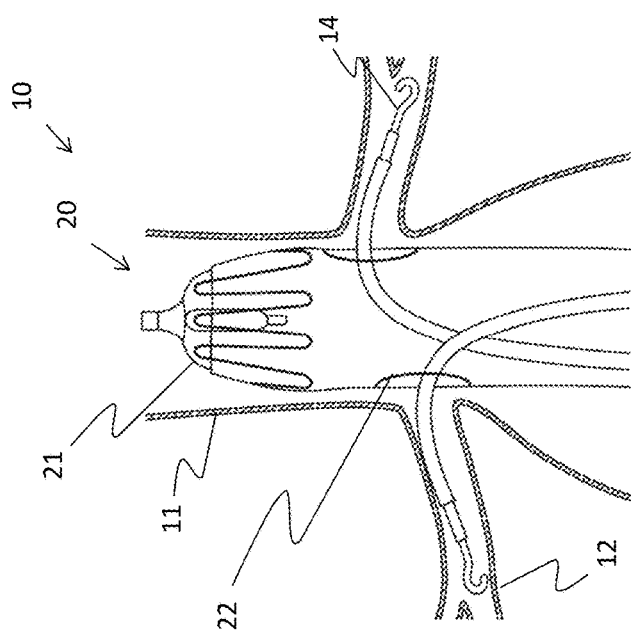
Figure 6:
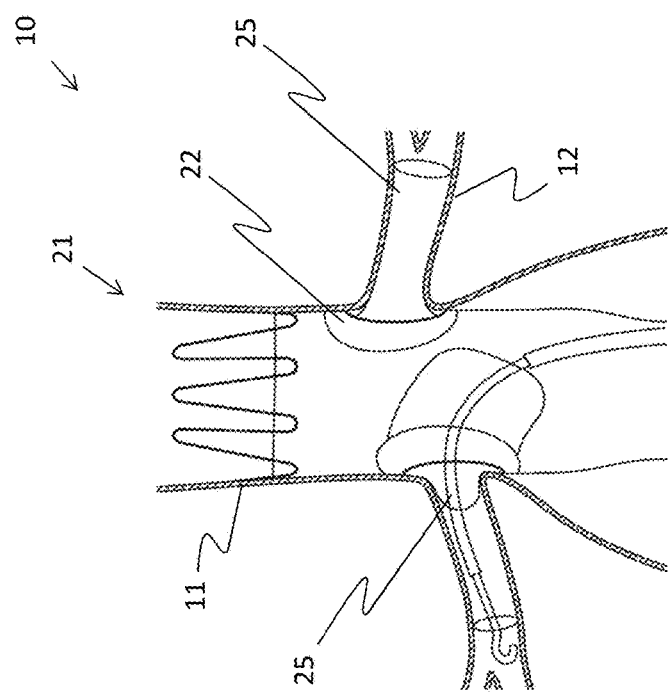

Reference is currently made to FIG. 11A, which is a cross-sectional view of Prior Art catheter 20 and stent 21, shown previously in FIGS. 3 and 4. Catheter 20 has an axially-configured guide wire and guide wire tube (referred hereinbelow to simply as "guide wire") 26, as known in the art. Prior art stent 21 (being crimped within the catheter) is typically positioned so that it occupies substantially the entire catheter inner diameter—indicated in the figure as "d". An unutilized region 122 is defined as the space between (crimped) stent 21 and the guide wire.

Reference is currently made to FIGS. 11B-11E, which are cross sectional views of catheters 120, 120a, and 120b having crimped stents 123 and 124 configured therein, in accordance with embodiments of the current invention. Catheter 120 has an axially-configured guide wire 126 (which is similar to the guide wire of prior art catheter 20, shown in of FIG. 11A). It is to be understood that catheter 120 shown in FIG. 11C and catheters 120a and 120b shown in FIGS. 11D and 11E, respectively, likewise have an axially-configured guide wire and sheath, not shown in the figures.

A significant aspect of the current invention is that the unutilized region may be more effectively utilized, such as—but not limited to: carrying additional stent/stent components that may be used for side deployment; and/or additional axial deployment, as described further hereinbelow.

As shown in FIGS. 11B and 11C, embodiments of the current invention having more effective stent designs and more effective stent crimping configurations (such as, but not limited to, the exemplary stent configurations shown hereinabove in FIGS. 7, 8, and 9) can allow a larger/more complicated crimped stent to assume an flattened, overlapping geometry, which may be carried within catheter 120 having a similar diameter to that of catheter 20, and thus utilize an unutilized region 122a—as shown in FIG. 11B—or allow a smaller/less complicated crimped stent 124 to be carried within the same catheter (FIG. 11C) and thus utilize an unutilized region 122b—thereby allowing additional space for other stents/stent components. Additionally or optionally, embodiments of the current invention allow for a smaller-diameter catheter 120a to be used to carry crimped stent 124, thereby more effectively utilizing unutilized region 122c—as shown in FIG. 11D. Additionally or optionally, as shown in FIG. 11E, embodiments of the current invention allow for a smaller-diameter catheter 120b to carry crimped stent 124 (having an overlapping geometry) to furthermore effectively utilize unutilized region 122d.

Reference is currently made to FIG. 12, which is a schematic side view of catheter 120 shown in FIG. 11B (with catheter tube removed for purposes of illustration), in accordance with embodiments of the current invention. A guide wire 126 extends from a V-tip at a distal end of the catheter (to the right in the figure). A side-delivery crimped stent system 130 has a crimped stent (also referred to hereinbelow as a "side stent") 132 positioned within the catheter, a pushing head 134, and a pushing cable 136. Catheter 120 is translated within a main blood vessel 140, the catheter being positioned substantially coaxially with the blood vessel. The side-delivery crimped stent system allows effective deployment of the side stent substantially perpendicular to the longitudinal axis the catheter/main blood vessel to a side blood vessel 142, which is typically inclined at an angle of at least 70 degrees with respect to a longitudinal axis of the main vessel 140.

Pushing cable 136 is controlled from the proximal end to control deployment of crimped stent 132. Additionally or optionally, side-delivery crimped stent system 130 make take advantage of a marker guide wire (not shown in the figure) included with pushing cable 136 to enable/enhance targeting of the correct location/direction for side stent deployment.

Reference is currently made to FIGS. 13A and 13B, which are schematic views of catheter 120 shown in FIG. 12, further indicating a main blood vessel 140 and a side blood vessel 142, having a larger than 70-degree orientation to the main blood vessel, in accordance with embodiments of the current invention. FIG. 13B additionally shows side stent 132 deployed into side blood vessel 142. Apart from differences described below, catheter 120 and side-stent delivery system 130 of FIG. 12 (hereinabove) are identical in notation, configuration, and functionality to that shown in FIGS. 13A and 13B, and elements indicated by the same reference numerals and/or letters are generally identical in configuration, operation, and functionality as described hereinabove.

Reference is currently made to FIGS. 14A and 14B, which are schematic views of the catheter shown in FIGS. 12 and 13, showing deployment of side stent 132 into side blood vessel 142, in accordance with embodiments of the current invention. Apart from differences described below, catheter 120 and stent 132 of FIGS. 13A and 13B (hereinabove) are identical in notation, configuration, and functionality to that shown in FIGS. 14A and 14B, and elements indicated by the same reference numerals and/or letters are generally identical in configuration, operation, and functionality as described hereinabove. Stent 132 in the current figures is shown having a fabric sealing dress, as known in the art. As shown in FIG. 14B, the catheter is positioned in main vessel 140 and four possible positional modes/movements are used to located and deploy the stent into side vessel 142, as follows:

$Z_1$: translational movement of the in a distal and proximal direction—ie along a catheter distal-proximal axis, otherwise referred to as a catheter longitudinal axis (not shown in the figures);

$\theta_1$: rotation of the catheter about its distal-proximal axis;

$Z_2$: translation movement of the side stent to and from the catheter; and $\theta_2$: rotation of the side stent "up" or "down" to align the side stent to the angle of side vessel 142.

Utilizing the above-mentioned four possible positional modes/movements, side stent 132 is effectively deployed into side vessel 142, having an inclination greater than 70 degrees with the axis of main vessel 140.

Viewing FIGS. 13A, 13B, 14A and 14B, a sequence of steps to position and deploy the side stent into the side blood vessel includes the following:

1. Translate and rotate the catheter ($Z_1$ and $\theta_1$ movement) within the main blood vessel to position the side stent delivery system across from the side blood vessel;
2. Partially deploy the side stent substantially perpendicularly from catheter longitudinal axis ($Z_2$ movement);
3. Rotate/steer the partially deployed side stent ($\theta_2$ movement) to align the side stent substantially concentrically with the side vessel;
4. Fully deploy the side stent into the side vessel ($Z_2$ movement); and
5. Repeat any of the $Z_1$, $Z_2$, $\theta_1$, and $\theta_2$ movements to complete full/proper deployment of the side stent into the side vessel.

As may be seen in FIGS. 14A and 14B, the technique/sequence of steps described hereinabove may be applied for two or more side vessels—as illustrated/discussed further hereinbelow.

Embodiments of the current invention using the configurations and techniques described hereinabove serve to effectively deliver and deploy an implant to a side vessel having an inclination greater than 70 degrees with the axis of main vessel, with no need to pass a catheter directly into the side vessel. The configurations and techniques described hereinabove thereby allowing fuller control of a bifurcation stent (ie "side stent") during deployment and thus afford more reliable results and concomitant lower risks in complicated geometries.

Embodiments of the current invention do not obviate additional/optional angioplasty balloon dilatation subsequent to the bifurcation stent being delivered to the desired location, for reasons such as, but not limited to: ensuring correct placement; and ensuring full deployment of the stent.

Reference is currently made to FIGS. 15A-15H, which are schematic representations of the aortic renal zone and the Juxtarenal Abdominal Aortic Aneurysm (AAA) shown hereinabove in FIG. 1C, with the current figures showing the sequence of steps for implant delivery in EVAR, in accordance with embodiments of the current invention. Apart from differences described below, Juxtarenal AAA 2c, catheter 120 and blood vessels 140 and 142 of FIG. 1C and FIGS. 13A,13B, 14A, and 14B (hereinabove) are identical in notation, configuration, and functionality to that shown in FIGS. 15A-15H, and elements indicated by the same reference numerals and/or letters are generally identical in configuration, operation, and functionality as described hereinabove. Side blood vessel 142 is referred to hereinbelow as first side blood vessel 142. Juxtarenal AAA 2c further shows/includes a secondary side vessel 144, a contralateral limb vessel 146, and ipsilateral limb vessel 148.

Catheter 120 is shown introduced to the AAA zone through contralateral limb vessel 146, as is typical in such procedures. Catheter 120 further includes a multi-stent delivery system 151, which is similar to side delivery crimp stent system 130 shown in FIGS. 12, 13A-B, and 14A-B— but with at least one side stent and at least one axially-deployed stent, the system having additional structure and functionality as described hereinbelow.

The term "multi-stent" as used in the description and claims hereinbelow is intended to mean a unified/singular configuration capable of deploying at least one side stent and at least one axially-deployed stent. The referred figures and the description which follows present an exemplary configuration having two side stents—specifically, a first side stent 152 and a second side stent 153—and an axially-deployed main stent 155; however, embodiments of the current invention are not limited to two side stents.

Figure 15H:
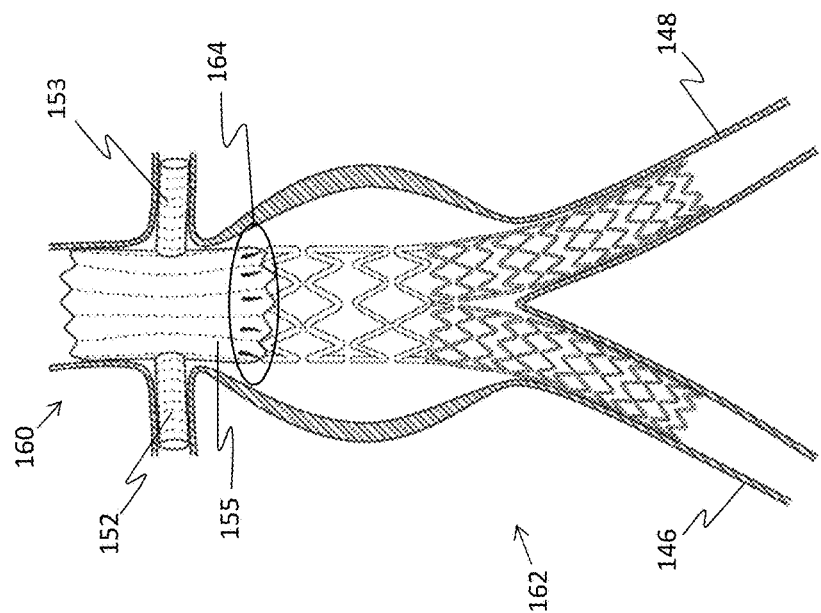

It is noted that whereas indicia are included and fully describe all elements shown in FIG. 15A, subsequent figures (ie FIGS. 15B-15H) having repetitive elements do not include repetitive indicia, for purposes of simplicity/clarity. Furthermore, the translation and rotational notations introduced in FIGS. 14A and 14B hereinabove, namely: $Z_1$; $\theta_1$; $Z_2$; and $\theta_2$, are referred to and apply to FIGS. 15A through 15G, mutatis mutandis.

Figure 15G:
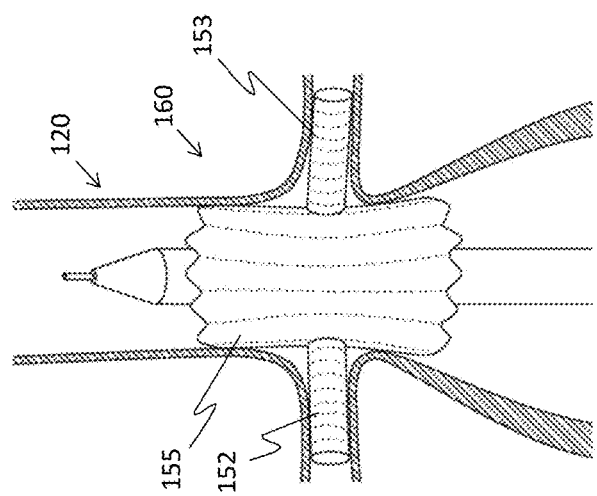

Referring specifically to FIGS. 15F and 15G, a deployed multi-stent configuration 160 is essentially the same as initial/deployed multi-stent configuration 38 shown hereinabove in FIG. 10A—however in the current figure, the multi-stent configuration is shown having a fabric sealing dress, as known in the art.

Figure 1A:
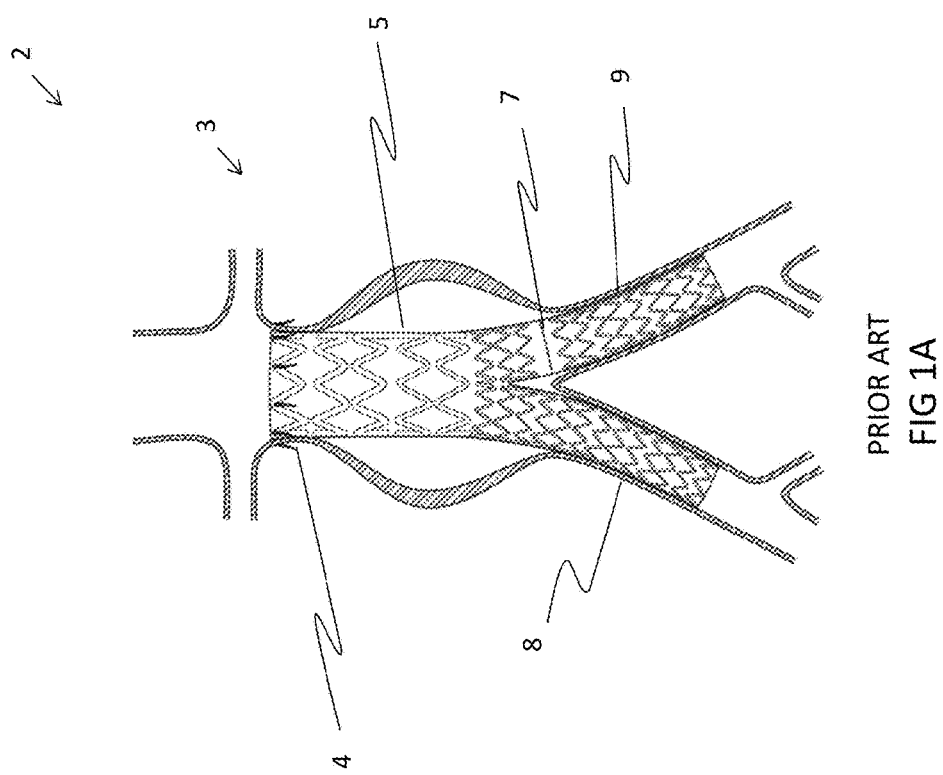
FIG. 1A is a schematic view of a typical aortic renal zone and an endovascular aneurysm (EVAR) repair Prior Art implant.

An implant 162, similar in every aspect to prior art implant 3 of FIG. 1A, is shown in FIG. 15H and is characterized, inter alia, by a plurality of fixation anchoring barbs 164 as shown in the figure. However, as opposed to prior art implant 3 where the barbs secure implant 3 to the main blood vessel, implant 162 uses the barbs to fix the implant to multi-stent configuration 160, as described further hereinbelow.

Implant 162, as described hereinabove with regard to prior art EVAR procedures, is shown in FIG. 15H without a fabric sealing dress for clarity; however, it is to be understood that implant 162 is likewise deployed having a fabric sealing dress as shown in FIG. 1A and as known in the art.

A sequence of steps for implant delivery in EVAR, including positioning and deployment of the multi-stent and the implant includes the following:

1. Translate and rotate the catheter (using respective $Z_1$ and $\theta_1$ movements) within the main blood vessel to position multi-stent delivery system 151 across from the first side blood vessel (FIG. 15A);
2. Partially deploy the first side stent substantially perpendicularly from a catheter longitudinal axis ($Z_2$ movement) in the direction of the first side blood vessel (FIG. 15B);
3. Rotate/steer the partially-deployed first side stent ($\theta_2$ movement) to align the first side stent substantially concentrically with the first side vessel;
4. Fully deploy the first side stent ($Z_2$ movement) into the first side vessel, repeating any of the $Z_1$, $Z_2$, $\theta_1$, and $\theta_2$ movements of the steps above to complete full/proper deployment of the first side stent into the first side vessel (FIG. 15C);
5. Repeat steps 2 through 4 above, mutatis mutandis, to partially and fully deploy the second side stent into the second side vessel (FIGS. 15D-15 E);
6. Deploy the main stent in the longitudinal direction ($Z_2$ movement) FIGS. 15F-15G, with previously-deployed side stents already having been secured with fenestrations in the main stent (not shown in the figure), thereby presenting the deployed multi-stent configuration, and then withdrawing the catheter; and
7. Deploying implant 162—in a separate procedure, as known in the art. The fixation barbs are currently applied to secure the implant directly to the multi-stent configuration—and not to the main blood vessel (as is the case with the barbs of prior art implant 3 of FIG. 1A).

It is noted that whereas the EVAR procedure described hereinabove is described and shown in FIGS. 15A-15H, as applied to a Juxtarenal AAA, the EVAR procedure described hereinabove may be effectively applied to an Infrarenal AAA and/or to Pararenal and Suprarenal AAAs (ref FIGS. 1D and 1E)—the latter two of which cannot effectively be repaired using current prior art methods due to, inter alia, the lack of a neck, as discussed hereinabove in FIGS. 1B-1E.

Reference is currently made to FIGS. 16A and 16B, which are a side and isometric views of a deployed multi-stent configuration 160 (similar to multi-stent configuration 38 shown in FIG. 10A) and isometric representations of three exemplary side stent deployed configurations 234, 235, and 236, in accordance with embodiments of the current invention. It is to be understood that side stent configurations 235 and 236c may replace side stent configuration 234 in multi-stent configuration 160.

Regarding the three exemplary side stent configurations, whereas the helical spring structure of side stent configuration 234 allows crimping primarily only in a longitudinal direction (ie "spring compression") side stent configurations 235 and 236 allow both longitudinally and radially crimping.

Reference is currently made to FIGS. 17A and 17B, which are schematic side and cross-sectional representations of a crimped multi-stent configuration 260, having a crimped main-stent configuration 239a similar to crimped main-stent configuration 39a shown in FIG. 10C, in accordance with embodiments of the current invention. Crimped side stents 234a are shown in the figures, crimped within crimped main-stent configuration 239a. It is to be understood that following deployment, crimped side stents 234a are equivalent to side stent deployed configuration 234. It is seen in the figures that crimped side stents 234a are positioned substantially coaxially within crimped main-stent configuration 239a.

Reference is currently made to FIGS. 18A and 18B, which are isometric views of a crimped multi-stent configuration 262, similar to crimped multi-stent configuration 260 shown in FIGS. 17A and 17B, and controlled side stent deployment systems 264, in accordance with embodiments of the current invention. Multi-stent configuration includes crimped main stent. Apart from differences described below, crimped main-stent configuration 239a shown in the current figures is identical in notation, configuration, and functionality to that shown in FIGS. 17A and 17B. Controlled side stent deployment system includes: exemplary crimped side stent 236a and deployment cord 266, which is laced into the crimped stent as shown in detail in FIG. 18A. (It is understood that crimped side stent 236a is the crimped configuration of side stent deployed configuration 236 shown in FIG. 16B. Cord 266, which is made of metallic and/or other materials known in the art, serves to both maintain crimped side stent 236a in a crimped state and to serve to controllably-release and subsequently deploy the side stent with the cord extending through the catheter to the controlling (ie proximal) end of the catheter, as known in the art.

Reference is currently made to FIGS. 19A-19D, which are schematic and sectional views of an initial-shape/deployed alternate multi-stent configuration 360 and a crimped alternate multi-stent configuration 362, in accordance with embodiments of the current invention. Deployed alternate multi-stent configuration 360 is similar to multi-sent configuration 160 shown in FIG. 16A, and crimped alternate multi-stent configuration 362 is similar to crimped multi-stent configuration 260 shown in in FIGS. 17A and 17B—with an exception, as noted hereinbelow.

As opposed to the crimped multi-stent configurations shown/described hereinabove, crimped alternate multi-stent configuration 362 (ref FIGS. 19C and 19D) includes two crimped side stents 364, which are configured in a direction substantially 90 degrees from the direction of side-stent deployment. As such, upon deployment, crimped side stents 364 are first rotated substantially 90 degrees and are then deployed as in the other configurations noted hereinabove, mutatis mutandis.

Embodiments of the current invention employ exemplary multi-stent configurations shown hereinabove—or variations thereof—the configurations having in common high utilization of the unutilized region, and thereby enabling deployment of the multi-stent in a unified/singular configuration, with side stents being deployed substantially 90 degrees from the catheter longitudinal axis, and where bifurcation inclinations are greater than 70 degrees relative to the longitudinal axis of the main vessel, and/or when the ratio of the main vessel diameter to at least one secondary vessel diameter is greater than 2.

It will be appreciated that the above descriptions are intended only to serve as examples, and that many other embodiments are possible within the scope of the present invention as defined in the appended claims.

The invention claimed is:

1. A method of delivering and deploying a multi stent using a multi stent delivery system for an intravascular bifurcation zone, the multi stent comprising a unified and singular configuration for deploying at least one side stent and at least one axially-deployed stent, the at least one side stent being part of a side stent delivery system, the bifurcation zone having a main blood vessel with a main blood vessel longitudinal axis and at least one side blood vessel branching out of the main blood vessel, wherein the bifurcation zone has at least one side blood vessel branching out of a main blood vessel, the method including the steps of:

taking a catheter having a catheter longitudinal axis substantially coaxial with the main blood vessel longitudinal axis, and having a tube coaxially-positioned within the catheter, the catheter having a distal end and a proximal end;

crimping the at least one side stent and at least one main stent to have respective configurations characterized by a substantially flattened, curved shape, and having an overlapping geometry, the crimped stents having a reduced cross-section within the sheath, to form a unified and singular configuration within a sheath, the sheath located substantially at the distal end;

operating the side stent delivery system to first deploy the at least one crimped side stent substantially normal to the catheter longitudinal axis and expanding the at least one side stent into the side blood vessel; and deploying the at least one crimpled main stent substantially along the catheter longitudinal axis, after deployment of the at least one side stent, and expanding the at least one main stent into the main blood vessel.

2. The method of claim 1, whereby the at least one side stent is deployed in the at least one side blood vessel having an inclination of at least 70 degrees with respect to the main blood vessel longitudinal axis.

3. The method of claim 2, whereby the multi stent is deployed in the main blood vessel and the at least one side blood vessel, the main blood vessel and the at least one side blood vessel having respective diameters, and a ratio of the respective diameters is at least 2.

4. The method of claim 3, whereby delivery and deployment of the multi stent is part of an endovascular aneurysm repair (EVAR) procedure and wherein the bifurcation zone includes a Juxtarenal Abdominal Aortic Aneurysm (AAA).

5. The method of claim 4, whereby the multi stent is delivered and deployed as part of one sub-procedure of the EVAR procedure, the sub-procedure including a singular insertion and associated withdrawal of the delivery system or components thereof, thereby serving to reduce a chronology of the procedure.

6. The method of claim 1, whereby delivery and deployment of the multi stent is part of an endovascular aneurysm repair (EVAR) procedure and wherein the bifurcation zone includes at least one aneurysm chosen from the group including: Pararenal AAA and Suprarenal AAA.

7. A method of delivering and deploying a multi stent comprising a main stent, a first side stent and a second side stent, located in a catheter having a tube coaxially-positioned therein, the catheter having a distal end and a proximal end, the catheter forming part of a multi stent delivery system for an intravascular bifurcation zone, and delivering and deploying the multi stent, as part of an endovascular aneurysm repair (EVAR) procedure, the bifurcation zone including a main blood vessel having a main blood vessel longitudinal axis and a first and a second side blood vessel the first and second blood vessels branching out of the main blood vessel, and the bifurcation zone further including at least one aneurysm chosen from the group including: Juxtarenal Abdominal Aortic Aneurysm (AAA), Pararenal AAA and Suprarenal AAA, whereby delivering and deploying the multi stent is performed as one sub-procedure of the EVAR procedure, the sub-procedure including a singular insertion and associated withdrawal of the delivery system or components thereof, the method including the steps of:

a. crimping the first side stent and the second side stent and the main stent to form a unified configuration within a sheath, the sheath located substantially at the distal end;

b. translating the catheter having a catheter longitudinal axis substantially coaxial with the main blood vessel longitudinal axis and rotating the catheter within the main blood vessel to position the multi-stent delivery system across from the first side blood vessel;

c. partially deploying the crimped first side stent substantially perpendicularly from the catheter longitudinal axis in the direction of the first side blood vessel;

d. rotating and steering the partially-deployed first side stent to align the first side stent substantially concentrically with the first side blood vessel;

e. fully deploying the first side stent into the first side blood vessel, repeating steps b-d to complete a full deployment of the first side stent into the first side vessel;

f. translating and rotating the catheter to position the multi-stent delivery system across from the second side blood vessel;

g. partially deploying the crimped second side stent substantially perpendicularly from the catheter longitudinal axis in the direction of the second side blood vessel;

h. rotating and steering the partially-deployed second side stent to align the second side stent substantially concentrically with the second side blood vessel;

i. fully deploying the second side stent into the second side blood vessel, repeating steps f-h to complete a full deployment of the second side stent into the second side vessel;

j. deploying the crimped main stent into the main blood vessel along the catheter longitudinal axis, the deployed main stent having lateral respective fenestrations corresponding to the first and second blood vessels and with the previously-deployed side stents secured in the respective fenestrations, thereby securing the multi stent in the bifurcation zone;

k. withdrawing the catheter; and l. deploying an implant in a separate sub-procedure and applying fixation barbs to secure the implant directly to the multi-stent configuration—and not to the main blood vessel.

\* \* \* \* \*